US010729164B2

(12) United States Patent
Shin et al.

(10) Patent No.: US 10,729,164 B2
(45) Date of Patent: Aug. 4, 2020

(54) IMMUNE-ENHANCING COMPOSITION COMPRISING ARABINOXYLAN FROM CORN OR CORN PROCESSING BY-PRODUCT

(71) Applicants: Kwang-Soon Shin, Seongnam-si, Gyeonggi-do (KR); SANDOL FOOD CO., LTD., Hongcheon-gun, Gangwon-do (KR); HONGCHEON INSTITUTE OF MEDICINAL HERB, Hongcheon-gun, Gangwon-do (KR)

(72) Inventors: Kwang-Soon Shin, Seongnam-si (KR); Sue-Jung Lee, Incheon (KR); Hye-Ryung Park, Seoul (KR); Sun Young Kim, Hongcheon-gun (KR); Dong-Joo Kwon, Chuncheon-si (KR); Ho-Sung Lee, Hongcheon-gun (KR)

(73) Assignees: Kwang-Soon Shin, Seongnam-si, Gyeonggi-Do (KR); SANDOL FOOD CO., LTD., Hongcheon-Gun, Gangwon-Do (KR); HONGCHEON INSTITUTE OF MEDICINAL HERB, Hongcheon-Gun, Gangwon-Do (KR)

( * ) Notice: Subject to any disclaimer, the term of this patent is extended or adjusted under 35 U.S.C. 154(b) by 0 days.

(21) Appl. No.: 15/771,272

(22) PCT Filed: Oct. 26, 2016

(86) PCT No.: PCT/KR2016/012099
§ 371 (c)(1),
(2) Date: Apr. 26, 2018

(87) PCT Pub. No.: WO2017/074031
PCT Pub. Date: May 4, 2017

(65) Prior Publication Data
US 2018/0325156 A1 Nov. 15, 2018

Related U.S. Application Data

(60) Provisional application No. PCT/KR2016/012099, filed on Oct. 26, 2016.

(30) Foreign Application Priority Data

Oct. 26, 2015 (KR) ........................ 10-2015-0149029

(51) Int. Cl.
*A23L 33/105* (2016.01)
*A61K 31/715* (2006.01)
*A23K 20/163* (2016.01)
*A23L 7/10* (2016.01)
*A61K 36/899* (2006.01)
*A23L 33/21* (2016.01)
*C08B 37/00* (2006.01)
*C08L 5/14* (2006.01)

(52) U.S. Cl.
CPC .......... *A23L 33/105* (2016.08); *A23K 20/163* (2016.05); *A23L 7/115* (2016.08); *A23L 33/21* (2016.08); *A61K 31/715* (2013.01); *A61K 36/899* (2013.01); *C08B 37/0057* (2013.01); *C08L 5/14* (2013.01); *A23V 2002/00* (2013.01); *A23V 2200/324* (2013.01); *A23V 2250/51* (2013.01)

(58) Field of Classification Search
None
See application file for complete search history.

(56) References Cited

U.S. PATENT DOCUMENTS

| 4,560,561 A * | 12/1985 | Henderson ............. A23K 40/20 426/454 |
| 2001/0020091 A1* | 9/2001 | Buchanan ............. A23D 9/007 536/123 |

FOREIGN PATENT DOCUMENTS

| KR | 1020100106289 A | 10/2010 |
| KR | 1020120095320 A | 8/2012 |
| KR | 101409213 B1 * | 6/2014 |
| KR | 1020140120808 A | 10/2014 |
| KR | 101535835 B1 | 7/2015 |

OTHER PUBLICATIONS

Izydorczyk, "Cereal arabinoxylans: advances in structure and physicochemical properties", Carbohydrate Polymers, 28, 33-48, 1995 (Year: 1995).*
Zhang, "Cereal-Derived Arabinoxylans as Biological Response Modifiers: Extraction, Molecular Features, and Immune-Stimulating Properties", Critical Reviews in Food Science and Nutrition, 55: 1033-1050, published online Oct. 14, 2014 (Year: 2014).*
English translation of KR101409213 B1 retrieved from Espacenet on Aug. 15, 2019 (Year: 2019).*
Saulnier et al., "Cell wall polysaccharide interactions in maize bran," Carbohydrate Polymers, 1995, vol. 26, pp. 279-287.
Ogawa et al., "Immunological Effects of Partially Hydrolyzed Arabinoxylan from Corn Husk in Mice," Bioscience, Biotechnology, and Biochemistry, 2005, vol. 69 (1), pp. 19-25.
Lee et al., "Macrophage-Stimulating Activity of Glucan-Rich Fraction Isolated from the Byproducts of Corn Starch Manufacturing Industry and Its Structural Characteristics," 2014 International Conference of the Korean Nutrition Society, Nov. 5, 2014, 3 pages.
Sue-Jung Lee, "Immuno-Stimulating Activity, Structural Characteristics and Action Mechanism of the Polysaccharides Isolated from the Byproducts of Starch Industries," Department of Food Science & Biotechnology Graduate School, Kyonggi University, MA. (MA.) Thesis, Jun. 1, 2015, 6 pages.
(Continued)

*Primary Examiner* — Robert T. Crow
*Assistant Examiner* — John P Nguyen
(74) *Attorney, Agent, or Firm* — Hauptman Ham, LLP

(57) ABSTRACT

The present invention relates to an immuno-enhancing composition including a corn-derived polysaccharide. The immuno-enhancing composition may be a food composition, a feed composition, or a pharmaceutical composition.

8 Claims, 20 Drawing Sheets

(56) References Cited

OTHER PUBLICATIONS

Lee et al., "Isolation of Macrophage-Stimulating Polysaccharide from the Byproducts of Corn Starch Manufacturing Industry and Its Structural Characterization," 2014 International Symposium and Annual Meeting Lifelong Health and Wellness from Nutrition and Food, Oct. 27, 2014, 3 pages.
Lee et al., "A Polysaccharide from the Byproducts of Starch Manufacturing Industry Activates Macrophages via MAPK and NF-k B Signal Pathways," 2015 KoSFoST International Symposium and Annual Meeting, Jun. 3, 2015, 3 pages.
Lee et al., "Structural Characteristics and Action Mechanism of the Immuno-Stimulating Polysaccharide Isolated from the Byproducts of Starch Industries," Phytonutrients and Healthy Foods, 2015 KFN International Symposium and Annual Meeting, Aug. 24, 2015, 9 pages.
International Search Report for PCT/KR2016/012099 dated Feb. 14, 2017.

\* cited by examiner

[FIG. 1]
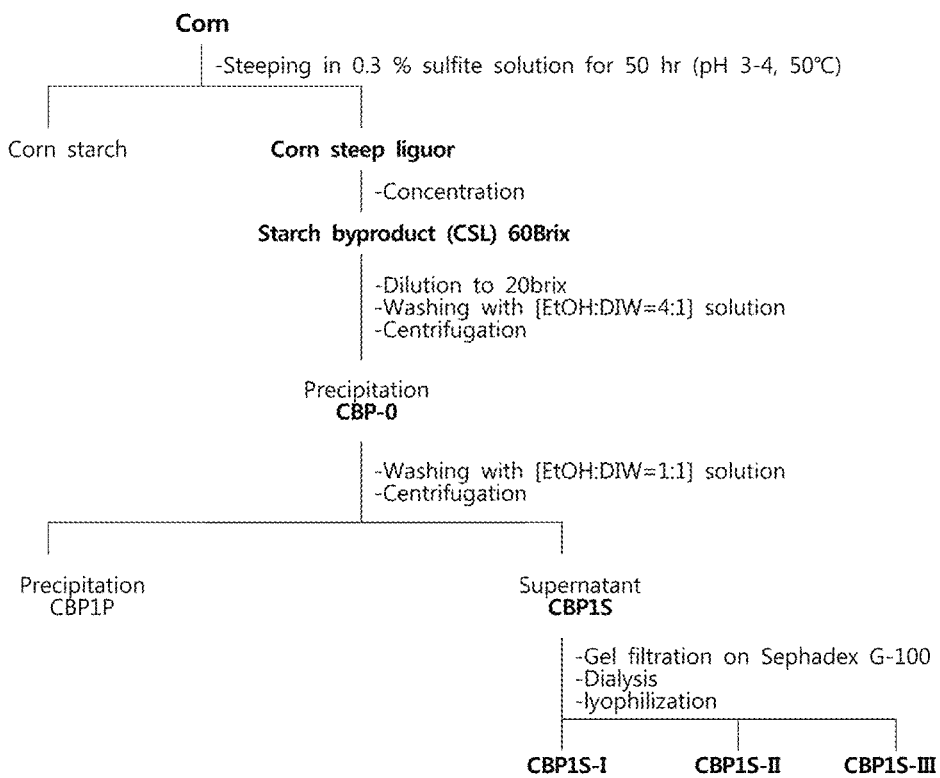
[FIG. 2]
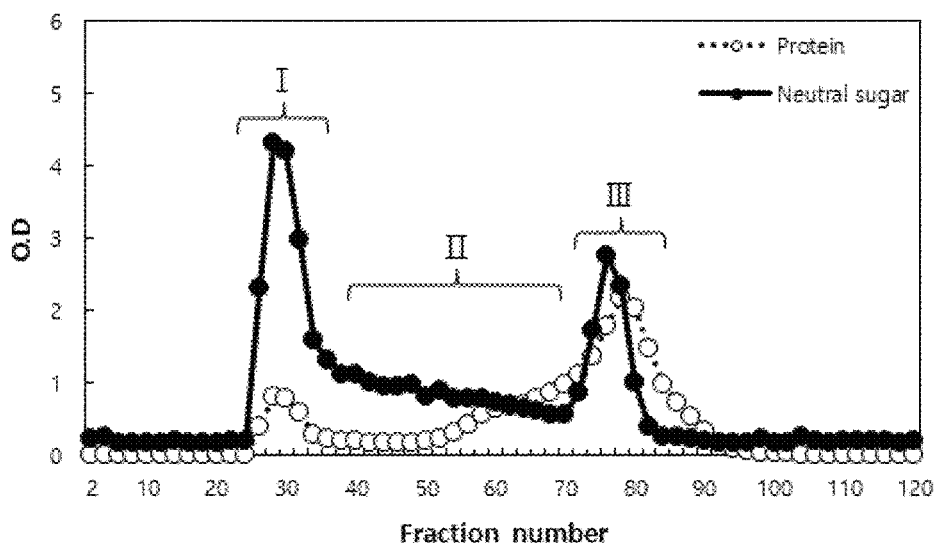

[FIG. 3]
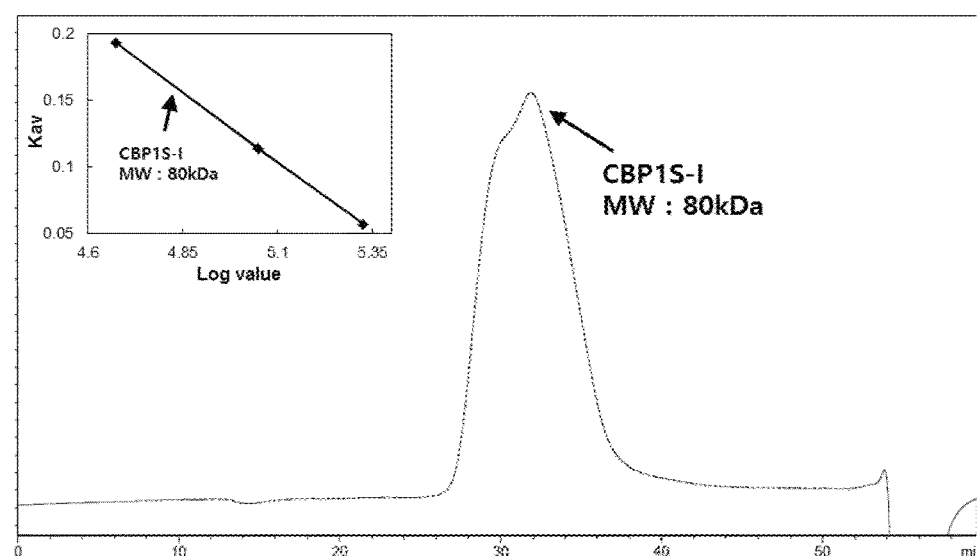

【FIG. 4a】
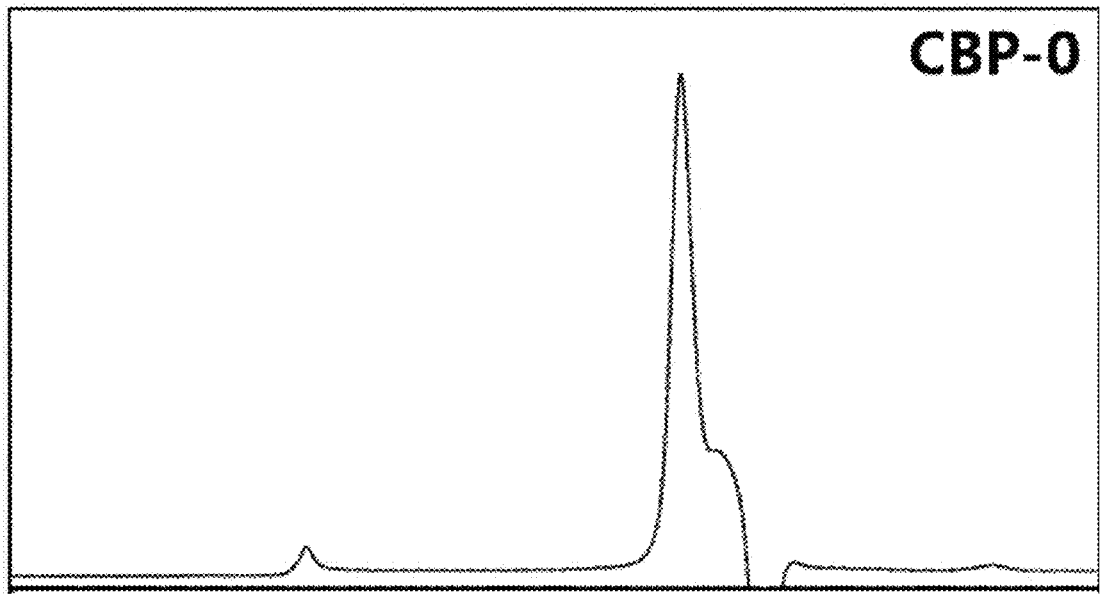
【FIG. 4b】
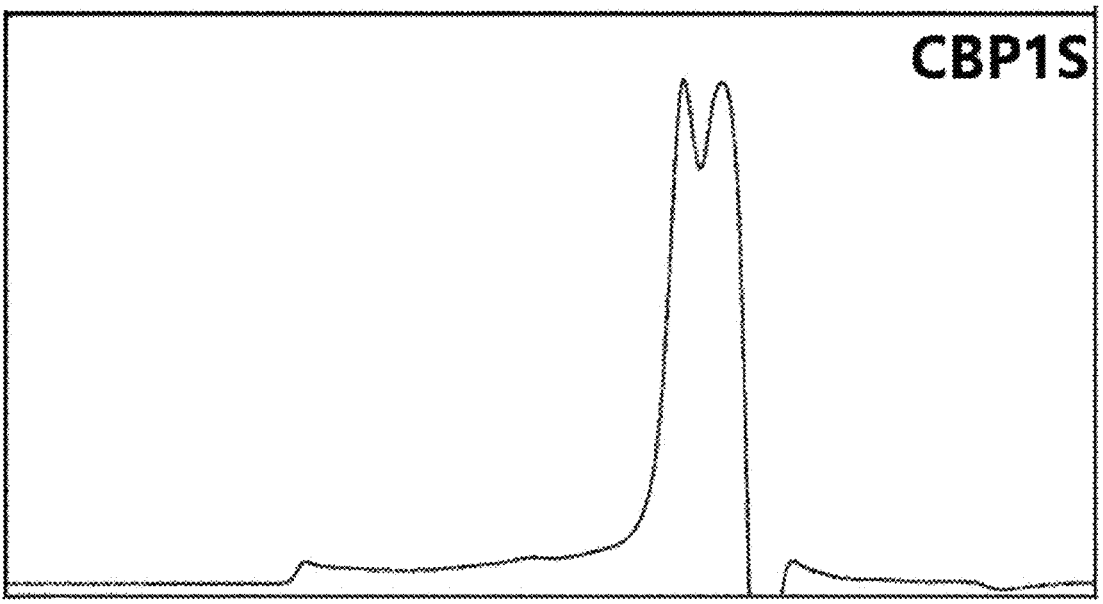

[FIG. 5a]
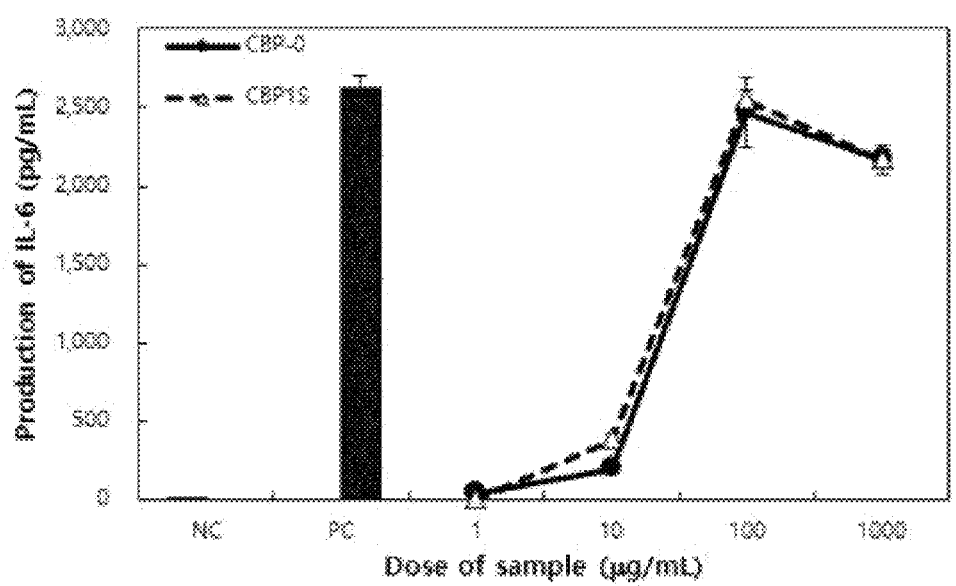
[FIG. 5b]
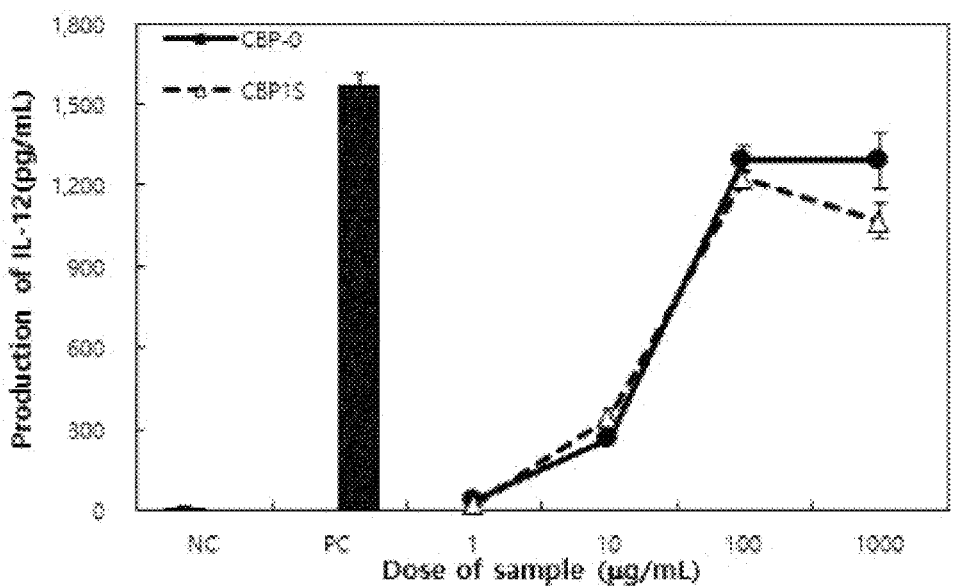

[FIG. 5c]
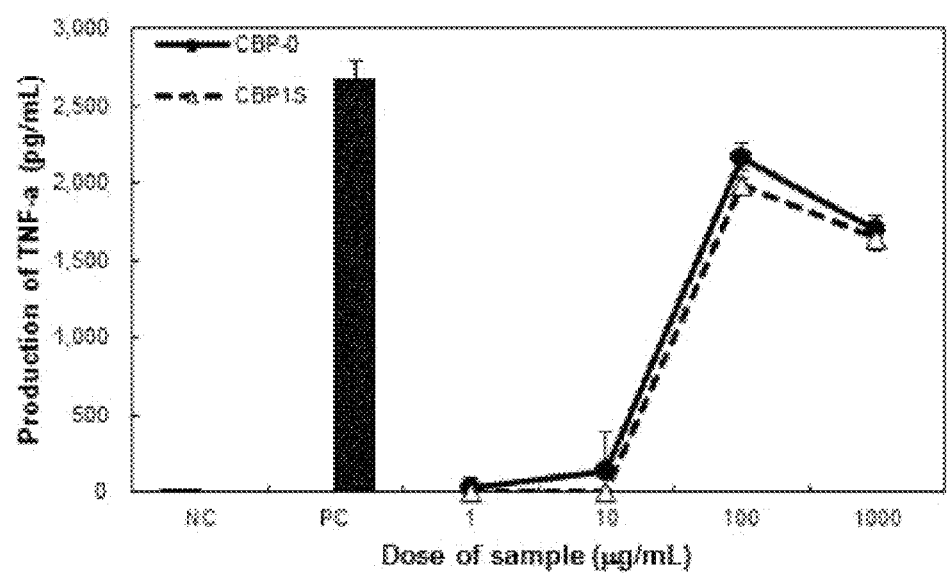

[FIG. 6]
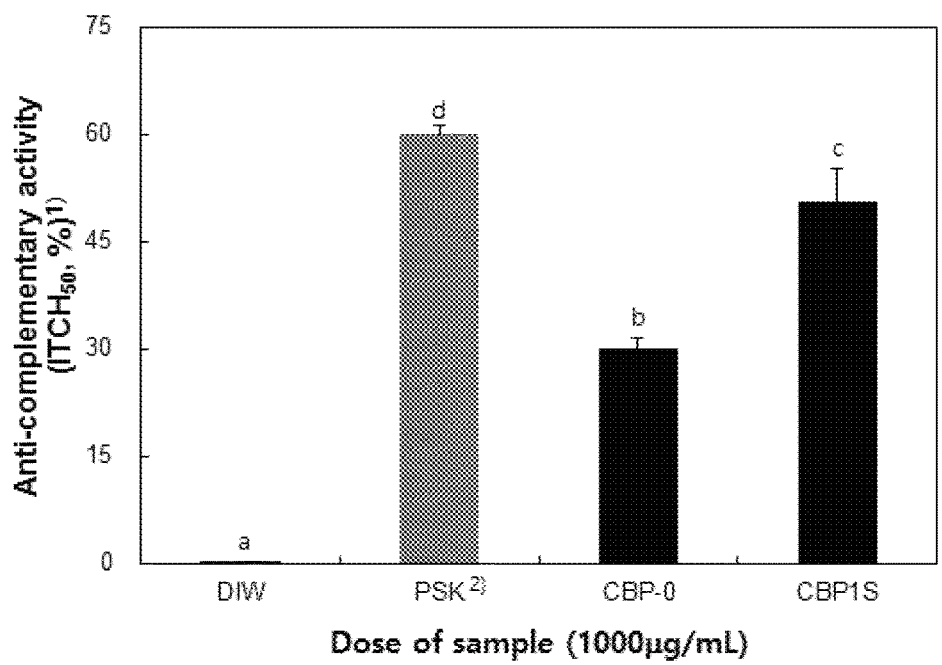

【FIG. 7a】
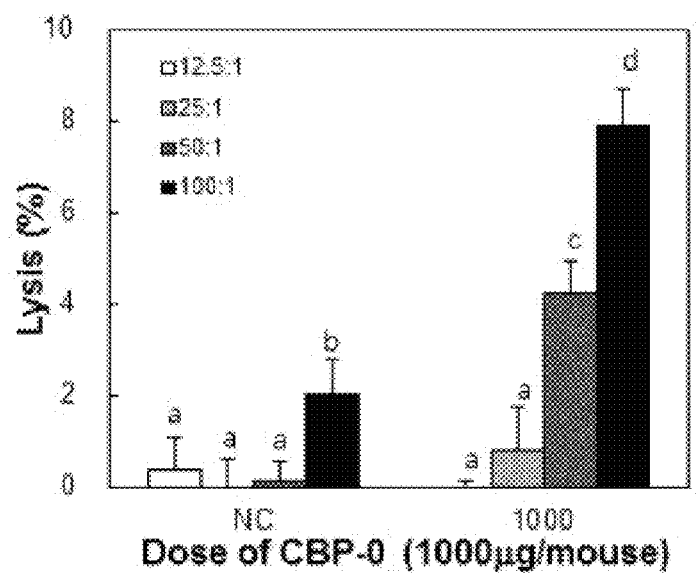
【FIG. 7b】
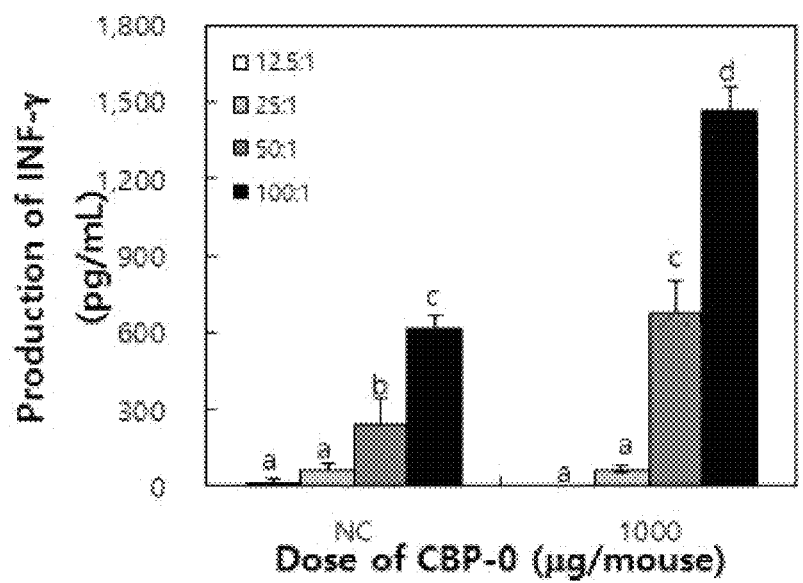

[FIG. 7c]
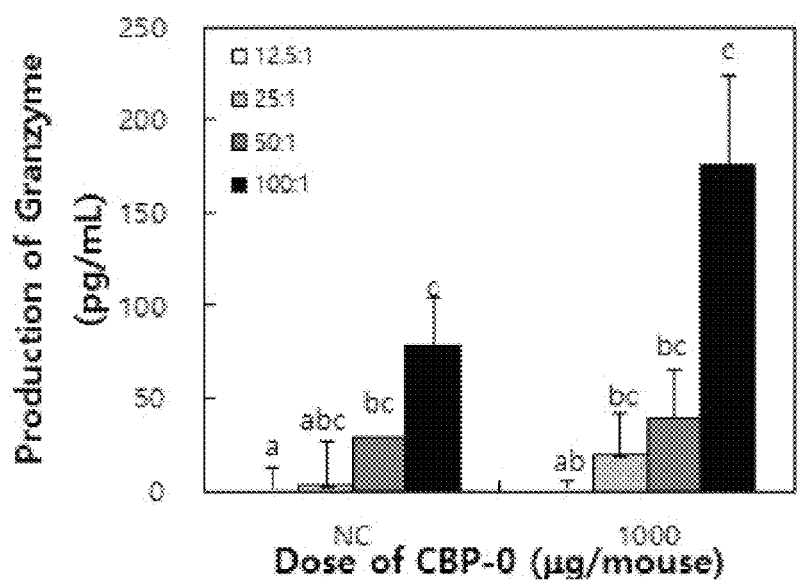

[FIG. 8a]
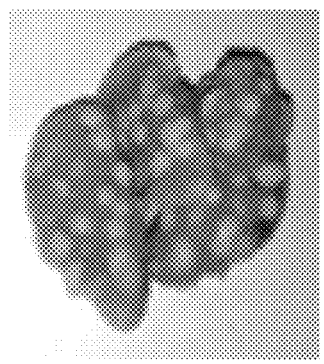
[FIG. 8b]
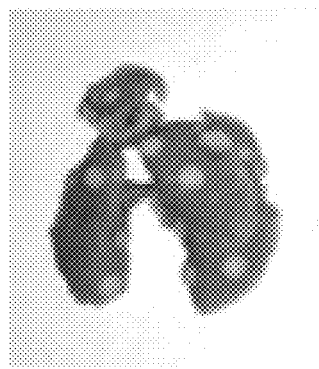

[FIG. 8c]
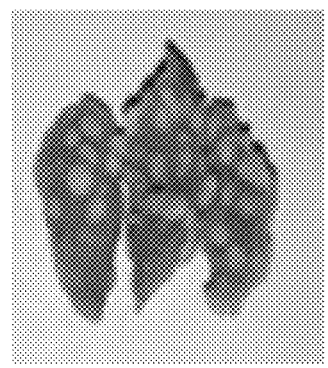
[FIG. 8d]
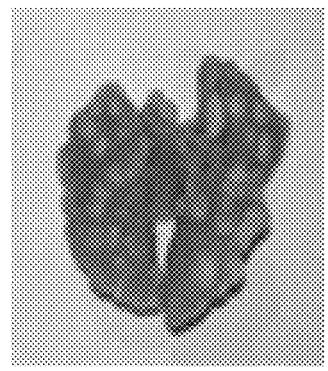

[FIG. 8e]
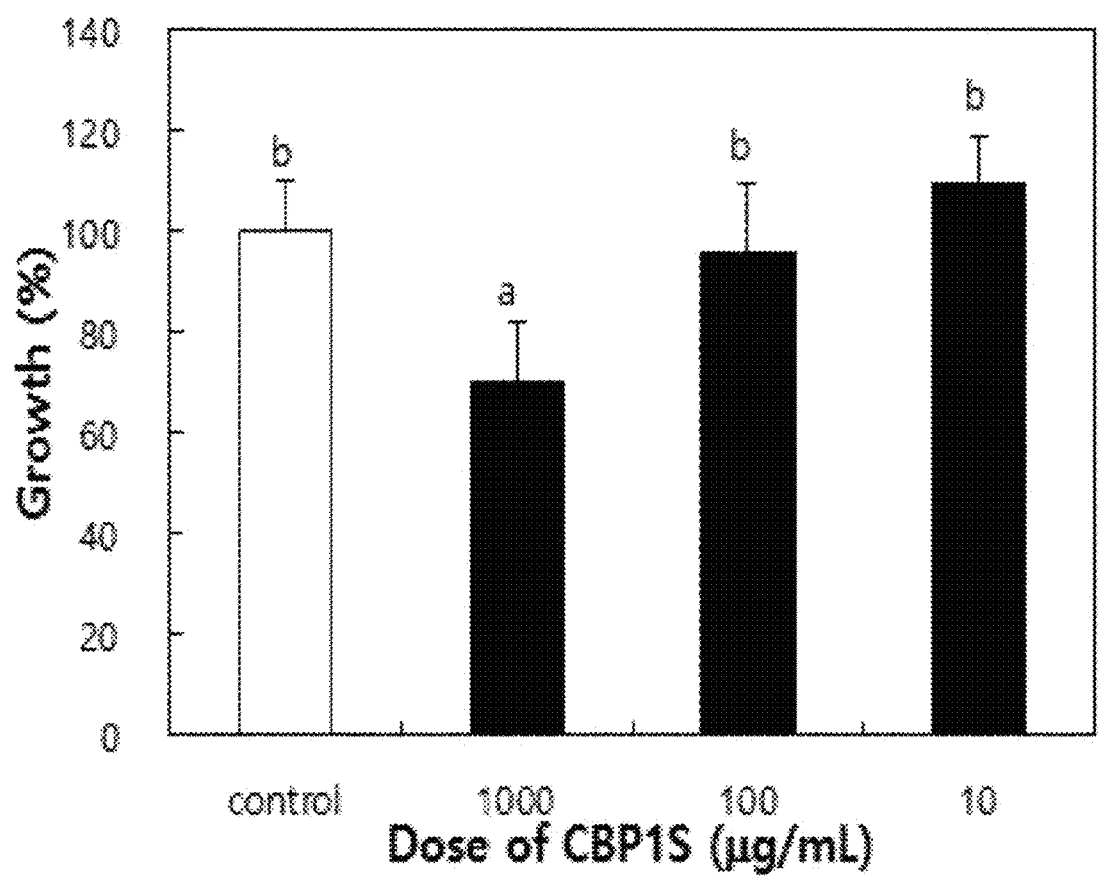

【FIG. 9a】
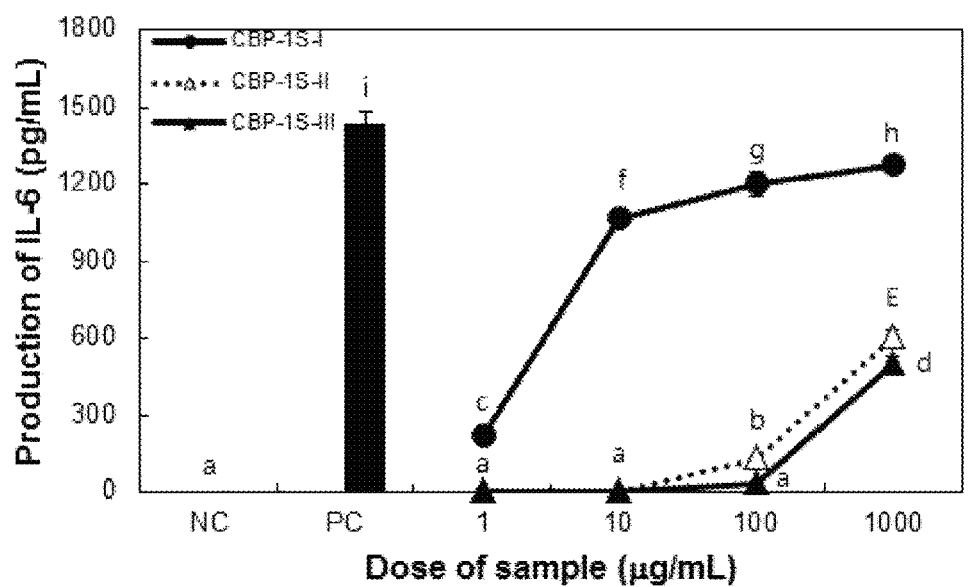
【FIG. 9b】
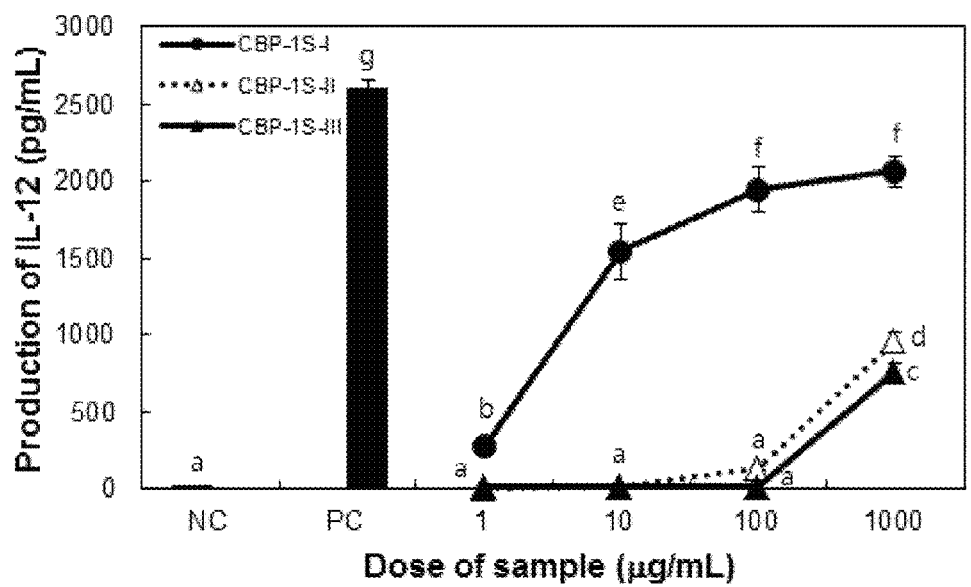

[FIG. 9c]
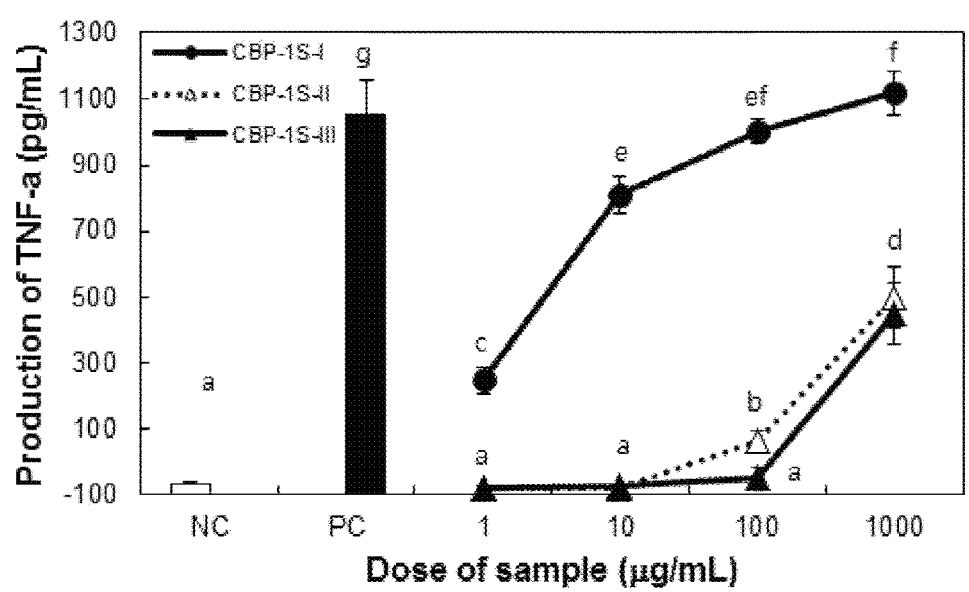

[FIG. 10]
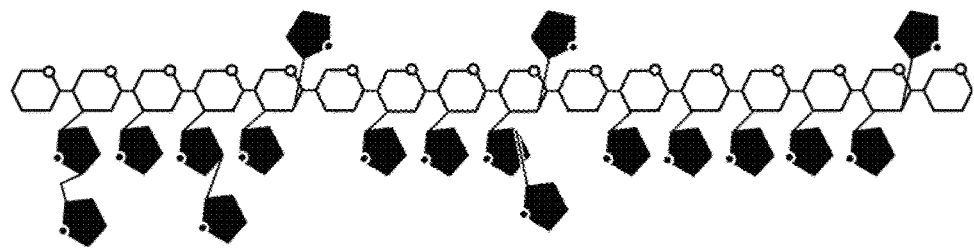
[FIG. 11]
CBP1S- I
- Endo-1,4-β-D-xylanase treatment (43°C, pH 6.5, 72 hr)
- Superdex 200 GL (1×30 cm, 0.5 mL/min)
- Desalting
- Lyophiligation
CBP1S-I-A      CBP1S-I-B      CBP1S-I-C 【FIG. 12】
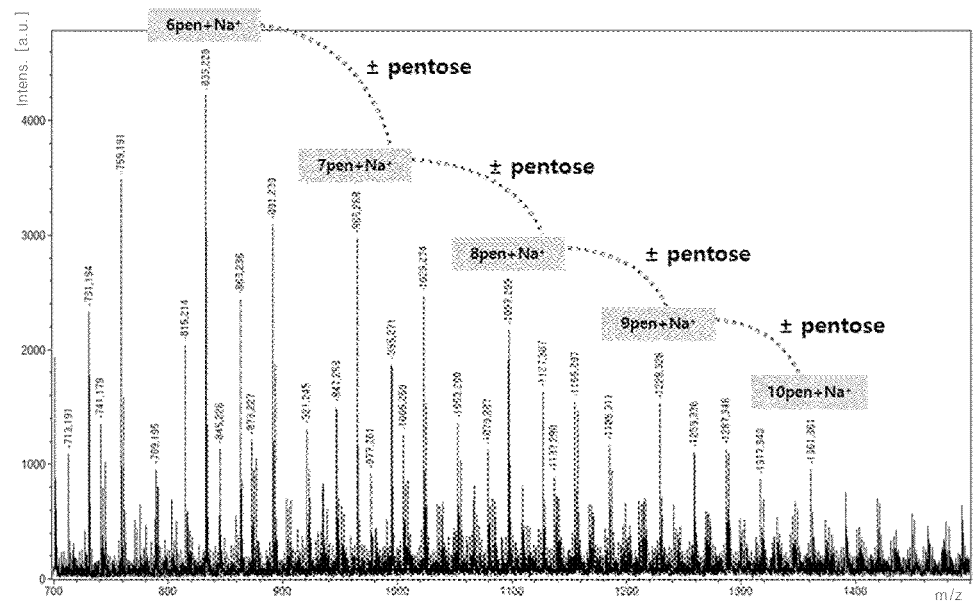
【FIG. 13】

[FIG. 14]
[FIG. 15]
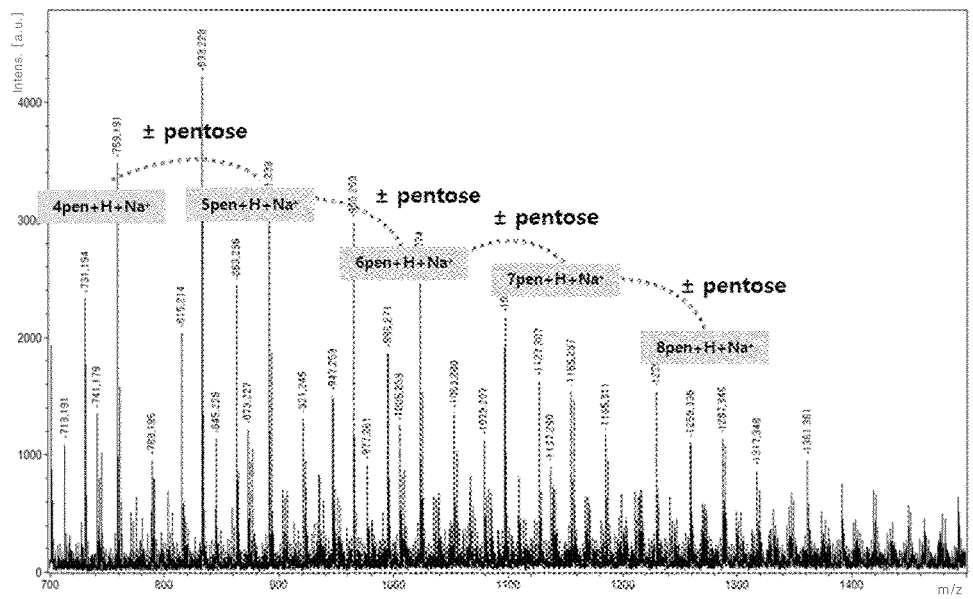

[FIG. 16]
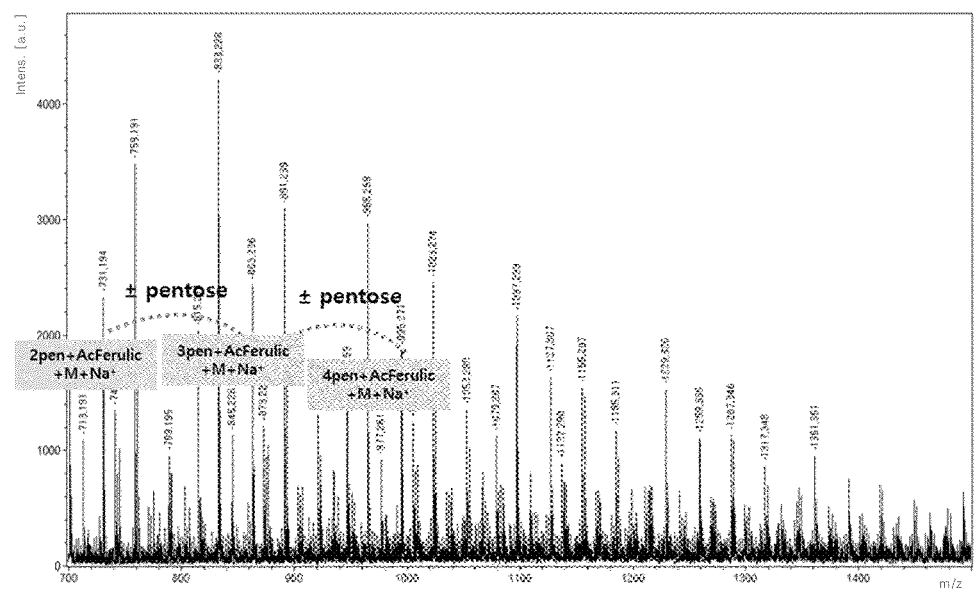
[FIG. 17]
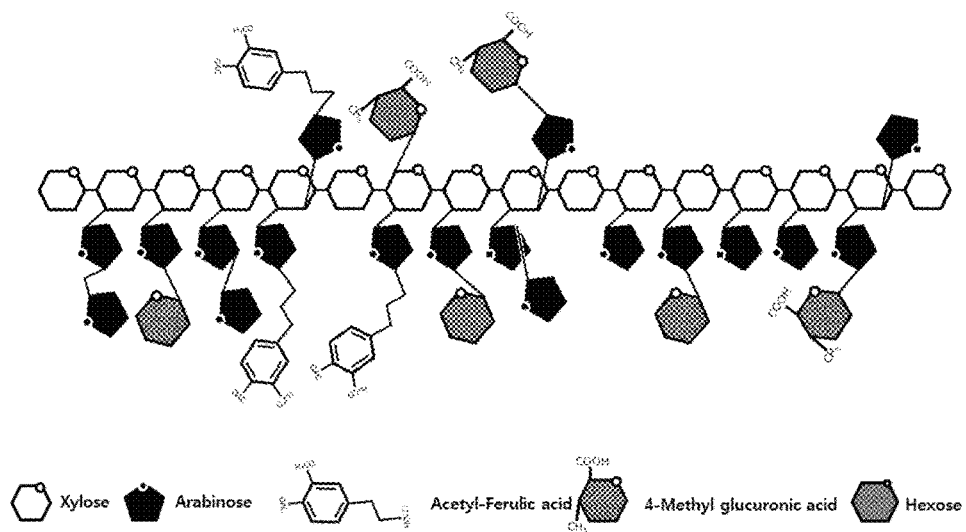

【FIG. 18a】
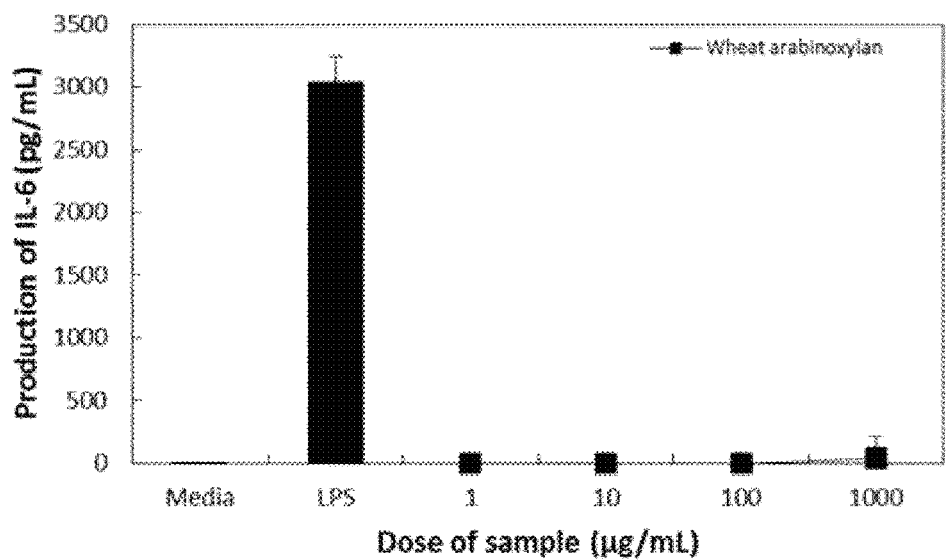
【FIG. 18b】
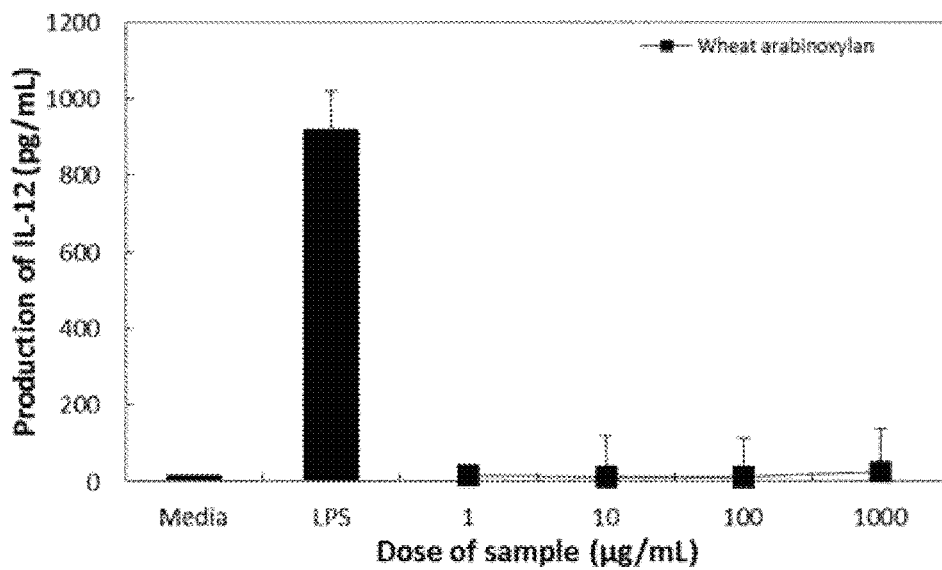

[FIG. 18c]
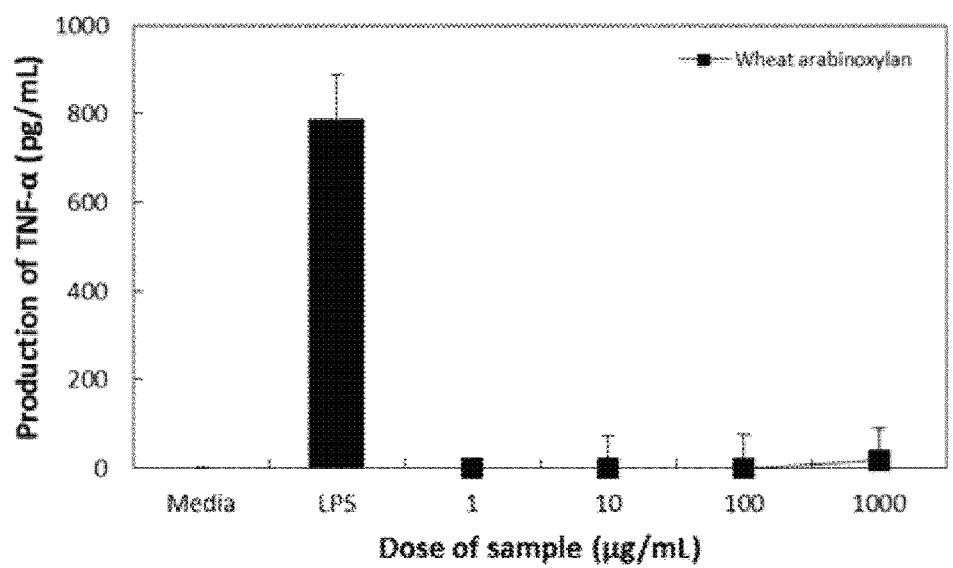

[FIG. 19]
Wheat arabinoxylan (no activity)
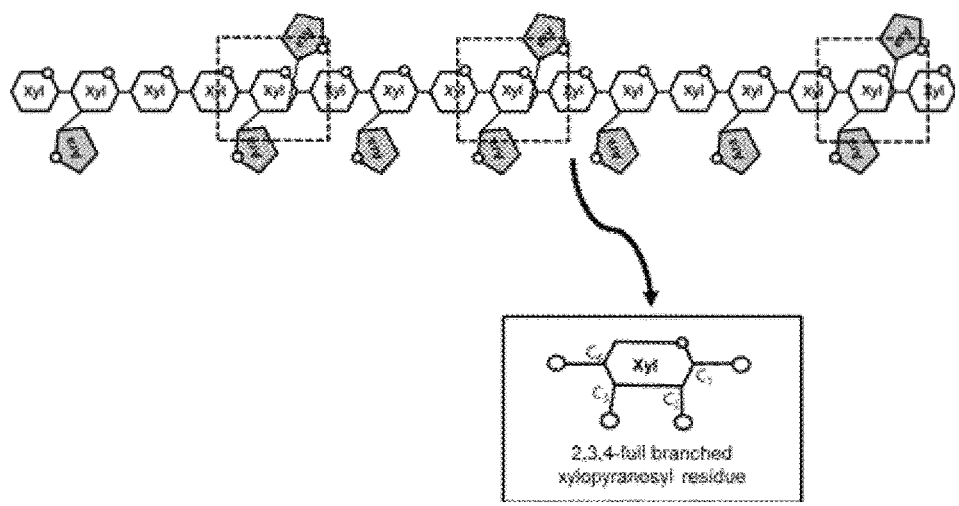

IMMUNE-ENHANCING COMPOSITION COMPRISING ARABINOXYLAN FROM CORN OR CORN PROCESSING BY-PRODUCT

TECHNICAL FIELD

The present invention relates to an immuno-enhancing composition including arabinoxylan derived from corn and a corn processing by-product.

BACKGROUND ART

Corn is a widely studied and used plant, such as starch is made from corn kernels, and an active ingredient has recently been extracted from corn silk (Korean Patent Registration No. 10-1535835). However, when certain products are manufactured using corn, by-products thereof are generated, and it is often difficult to treat them.

For example, when corn starch is produced, corn steep liquor (CSL), and a corn germ portion and pericarp (bran), which are removed during extraction, are generated as by-products. In a liquid in which the immersion of raw materials has been completed, most of the soluble materials in corn are eluted, insoluble materials are partially extracted by cleavage and/or modification, and a large amount of lactic acid fermented by the eluted saccharides is contained. According to a report, the immersion-completed liquid is concentrated into CSL, and the liquid contains a large amount of carbohydrates, amino acids, peptides, vitamins, essential minerals, and phytic acid, which is known as an antioxidant of natural plants, and thus CSL is used as an organic nitrogen source with excellent nutrients in the fermentation industry and a part of it is used for feed. However, since CSL is present in a liquid phase having a very high viscosity, it is inconvenient in handling, and although a part of CSL is used as a medium for fermentation and a feedstuff, in most corn starch factories, a large amount of produced CSL is discharged into the sea at high cost due to a high chemical oxygen demand (COD) load caused when discharged as wastewater. However, the disposal of CSL has become a serious problem due to a complete ban by legal sanctions since 2016.

In addition, in the case of corn pericarp among by-products generated when starch is prepared from corn, it has been reported that phytosterol, which lowers cholesterol levels, is contained in oil components of the corn pericarp, and the content of arabinoxylan in corn pericarp and the structure, properties, and efficacy of corn pericarp have also been reported. However, research on CSL, which is a by-product produced when corn starch is prepared, is lacking, and this is especially true for research on polysaccharides contained in CSL.

Meanwhile, macrophages are cells which secrete various cytokines and regulate immune conditions during a process of engulfing and digesting microorganisms or foreign matter, and play a vital role in immune responses against antigens, and macrophages are involved in antigen presentation and a non-specific immune function of lymphocytes, and exhibit direct cytotoxicity on tumor cells. In addition, it is known that materials responding to toll-like receptors (TLRs) such as LPS or natural materials activate macrophages, leading to the proliferation of T cells and B cells, the activation of macrophages for phagocytosis, and the production of cytokines such as IL-1, IL-6, IL-12, and TNF-α, which are capable of regulating a secondary immune response such as a defense against microorganism infections. IL-6 and TNF-α, which are representative cytokines induced by macrophages, are known to play a pivotal role in the inflammatory response to bacterial infections and increase quantitatively in inflammatory lesions. IL-6 and IL-1 have been reported to be involved in the differentiation of T cells and B cells by cooperative action and have anti-cancer effects, and TNF-α has been known to have cytotoxic and antiviral actions on specific cancer cells and play an important role in various biological reactions occurring in acute and chronic inflammatory diseases. Meanwhile, IL-12, which is a cytokine that induces NK cell activation and Th1-type immune responses, is known to increase reactivity with foreign cells such as cancer cells.

As a result of having studied the use of by-products generated when corn starch is prepared, the inventors of the present invention discovered that specific polysaccharides separated from CSL were included in the CSL in a cleaved and modified state by sulfurous acid treated in a starch preparation process, and also identified its immuno-enhancing activity, thus completing the present invention based on the findings.

DISCLOSURE

Technical Problem

An object of the present invention is to provide an immuno-enhancing composition.

Technical Solution

In accordance with an aspect of an embodiment, the present invention provides an immuno-enhancing composition including a corn-derived polysaccharide.

Advantageous Effects

An immuno-enhancing composition of the present invention has a cytokine secretion-enhancing ability, an ability to enhance the activity of natural killer cells, and a tumor metastasis-inhibiting ability.

DESCRIPTION OF DRAWINGS

FIG. 1 illustrates a process of separating and purifying polysaccharides from corn.

FIG. 2 illustrates gel permeation results of a CBP1S fraction on a Sephadex G-100 column, wherein CBP1S was treated on a Sephadex G-100 column (2.5 cm×90 cm) and eluted with a 50 mM ammonium formate buffer (pH 5.5) at a rate of 1 ml/min.

FIG. 3 illustrates an elution pattern and molecular weight (MW)-determination of CBP1S-I purified from CBP1S-I on size exclusion HPLC, wherein the HPLC was equipped with Asahi-Pak GS-520+GS-320+GS-220-linked columns.

FIG. 4a illustrates an elution pattern of CBP-0 separated from corn and corn processing by-products on size exclusion HPLC, wherein the HPLC was equipped with Superdex 200 GL columns. FIG. 4b illustrates an elution pattern of CBP1S separated from corn and corn processing by-products on size exclusion HPLC, wherein the HPLC was equipped with Superdex 200 GL columns.

FIG. 5a illustrates the effects of CBP-0 and CBP1S on IL-6s by murine peritoneal macrophages. FIG. 5b illustrates the effects of CBP-0 and CBP1S on IL-12 by murine peritoneal macrophages. FIG. 5c illustrates the effects of CBP-0 and CBP1S on TNF-α by murine peritoneal macrophages.

FIG. 6 illustrates anti-complementary activities of CBP-0 and CBP1S separated from corn and corn processing by-products, wherein 1) the anti-complementary activity was expressed as inhibition of 50% total complementary hemolysis using a Mayer method; 2) polysaccharide K (PSK), which is an immunologically active polysaccharide derived from Coriolus versicolor, was used as a positive control; and averages with different superscripts (a-c) show a significant difference of $p<0.05$ when subjected to a Duncan's multiple range test.

FIG. 7a illustrates the effect of CBP-0 on cell killing activity of NK cells ex vivo through lysis, wherein the NK cells were incubated along with a YAC-I target in a $CO_2$ incubator at 37° C. for 24 hours or 6 hours in the presence or absence of CBR0; and averages with different superscripts (a-d) show a significant difference of $p<0.05$ when subjected to a Duncan's multiple range test. FIG. 7b illustrates the effect of CBP-0 on cell killing activity of NK cells ex vivo through the production of INF-γ, wherein the NK cells were incubated along with a YAC-I target in a $CO_2$ incubator at 37° C. for 24 hours or 6 hours in the presence or absence of CBR0; and averages with different superscripts (a-d) show a significant difference of $p<0.05$ when subjected to a Duncan's multiple range test. FIG. 7c illustrates the effect of CBP-0 on cell killing activity of NK cells ex vivo through the production of granzyme, wherein the NK cells were incubated along with a YAC-I target in a $CO_2$ incubator at 37° C. for 24 hours or 6 hours in the presence or absence of CBP-0; and averages with different superscripts (a-d) show a significant difference of $p<0.05$ when subjected to a Duncan's multiple range test.

FIG. 8a illustrates the effect of control on lung metastasis made by intravenous (i.v.) inoculation of Colon 26-M3.1 carcinoma cells, wherein 4 BALB/c mice per group were orally administered CBP1S at a predetermined dose, followed by intravenous inoculation with $3\times10^4$ Colon 26-M3.1 carcinoma cells; The mice were sacrificed 14 days after the tumor inoculation to evaluate the tumors; and averages with different superscripts (a-b) show a significant difference of $p<0.05$ when subjected to a Duncan's multiple range test. FIG. 8b illustrates the effect of CBP1S 1000 μg/mL oral administration on lung metastasis made by intravenous (i.v.) inoculation of Colon 26-M3.1 carcinoma cells, wherein 4 BALB/c mice per group were orally administered CBP1S at a predetermined dose, followed by intravenous inoculation with $3\times10^4$ Colon 26-M3.1 carcinoma cells; The mice were sacrificed 14 days after the tumor inoculation to evaluate the tumors; and averages with different superscripts (a-b) show a significant difference of $p<0.05$ when subjected to a Duncan's multiple range test. FIG. 8c illustrates the effect of CBP1S 100 μg/mL oral administration on lung metastasis made by intravenous (i.v.) inoculation of Colon 26-M3.1 carcinoma cells, wherein 4 BALB/c mice per group were orally administered CBP1S at a predetermined dose, followed by intravenous inoculation with $3\times10^4$ Colon 26-M3.1 carcinoma cells; The mice were sacrificed 14 days after the tumor inoculation to evaluate the tumors; and averages with different superscripts (a-b) show a significant difference of $p<0.05$ when subjected to a Duncan's multiple range test. FIG. 8d illustrates the effect of CBP1S 10 μg/mL oral administration on lung metastasis made by intravenous (i.v.) inoculation of Colon 26-M3.1 carcinoma cells, wherein 4 BALB/c mice per group were orally administered CBP1S at a predetermined dose, followed by intravenous inoculation with $3\times10^4$ Colon 26-M3.1 carcinoma cells; The mice were sacrificed 14 days after the tumor inoculation to evaluate the tumors; and averages with different superscripts (a-b) show a significant difference of $p<0.05$ when subjected to a Duncan's multiple range test. FIG. 8e illustrates the effect of CBP1S oral administration on lung metastasis made by intravenous (i.v.) inoculation of Colon 26-M3.1 carcinoma cells via graph, wherein 4 BALB/c mice per group were orally administered CBP1S at a predetermined dose, followed by intravenous inoculation with $3\times10^4$ Colon 26-M3.1 carcinoma cells; The mice were sacrificed 14 days after the tumor inoculation to evaluate the tumors; and averages with different superscripts (a-b) show a significant difference of $p<0.05$ when subjected to a Duncan's multiple range test.

FIG. 9a illustrates the effects of CBP1S-I, CBP1S-II, and CBP1S-III on IL-6 produced by murine peritoneal macrophages, wherein averages with different superscripts (a-e) show a significant difference of $p<0.05$ when subjected to a Duncan's multiple range test. FIG. 9b illustrates the effects of CBP1S-I, CBP1S-II, and CBP1S-III on IL-12 produced by murine peritoneal macrophages, wherein averages with different superscripts (a-e) show a significant difference of $p<0.05$ when subjected to a Duncan's multiple range test. FIG. 9c illustrates the effects of CBP1S-I, CBP1S-II, and CBP1S-III on TNF-α produced by murine peritoneal macrophages, wherein averages with different superscripts (a-e) show a significant difference of $p<0.05$ when subjected to a Duncan's multiple range test.

FIG. 10 illustrates a possible structure of CBP1S-I, which is purified from CBP1S and is a polysaccharide having immuno-enhancing activity, and a chemical structure of arabinoxylan.

FIG. 11 illustrates an enzyme treatment process for the structural analysis of CBP1S-I.

FIGS. 12 to 16 illustrate possible structures of CBP1S-I-C purified from CBP1S and MALDI-TOF spectra, wherein FIG. 12 illustrates analysis results of m/z 833 [P6+Na]+ peaks; FIG. 13 illustrates analysis results of m/z 759 [P4+M+Na]+ peaks; FIG. 14 illustrates analysis results of m/z 731 [P4+H+Na]+ peaks; FIG. 15 illustrates analysis results of m/z 741 [P+Acf+Na]+ peaks; FIG. 16 illustrates analysis results of m/z 713 [P+M+Acf+Na]+ peaks; and in FIGS. 12 to 16, P=pentose oligomers; AcFerulic=acetyl ferulic acid; M=4-methyl-glucuronic acid; H=hexose.

FIG. 17 illustrates a possible detailed structure of CBP1S-I, which is a polysaccharide having immuno-enhancing activity.

FIG. 18a illustrates the effect of wheat-derived arabinoxylan on IL-6 by murine peritoneal macrophages. FIG. 18b illustrates the effect of wheat-derived arabinoxylan on IL-12 by murine peritoneal macrophages. FIG. 18c illustrates the effect of wheat-derived arabinoxylan on TNF-α by murine peritoneal macrophages.

FIG. 19 illustrates a chemical structure of wheat-derived arabinoxylan.

BEST MODE

The present invention relates to an immuno-enhancing composition including a corn-derived polysaccharide.

Hereinafter, the present invention will be described in detail.

Corn-Derived Polysaccharide

The present invention relates to an immuno-enhancing composition including a corn-derived polysaccharide.

The corn may be corn kernels or a by-product thereof. The by-product refers to a corn-derived by-product produced during a core processing process including preferably acid treatment, more preferably sulfurous acid treatment. The by-product may be a corn-derived by-product generated in a process of preparing starch from corn, preferably corn steep liquor (CSL) generated in a starch preparation process, but the present invention is not limited to the above examples. For example, the corn-derived polysaccharide of the present invention is a polysaccharide modified by acid treatment, preferably sulfurous acid treatment so as to have a structure different from natural polysaccharides contained in corn.

The polysaccharide of the present invention is a corn-derived polysaccharide. The polysaccharide may be arabinoxylan, which preferably contains 8 wt % or more of arabinose and xylose, more preferably contains 20 wt % or more of arabinose and xylose, and most preferably contain 50 wt % or more of arabinose and xylose.

Although the polysaccharide of the present invention is a corn-derived polysaccharide, it has a structure and/or activity different from that of polysaccharides naturally present in corn. This is because the structure and/or activity of the polysaccharide are/is modified in corn processing, and the present invention relates to the modified polysaccharide.

The polysaccharide of the present invention may be prepared by separation and purification according to a preparation method of CBP-0, CBP1S, or CBP1S-I, which will be described in the following examples, but the present invention is not limited thereto.

The polysaccharide of the present invention is arabinoxylan, which is a polysaccharide including xylan in a main chain thereof and arabinose in a side chain thereof. Preferably, the polysaccharide of the present invention includes xylan, in which xylose residues are linked by a (1→4) bond, in a main chain thereof, and has a single side chain linked at the C3 position of xylose or two side chains linked at the C2 and C3 positions of xylose, wherein the side chain(s) includes arabinose. At this time, the arabinose may be linked with 4-methyl-gluconic acid, acetic ferulic acid, or a hexose at a terminal thereof.

The polysaccharide of the present invention increases the secretion of interleukin-6, interleukin-12, or TNF-alpha (TNF-α), enhances the activity of natural killer cells, and inhibits tumor metastasis.

Immuno-Enhancing Composition

The present invention relates to an immuno-enhancing composition including a corn-derived polysaccharide. The immuno-enhancing composition may be a food composition, a pharmaceutical composition, or a feed composition.

Food Composition

A food of the present invention includes a health food supplement, a health functional food, a functional food, and an exercise supplement, but the present invention is not limited thereto. In addition, the food of the present invention also includes a natural food, a processing food, a general food material, or the like to which the corn-derived polysaccharide of the present invention is added.

A food composition including the corn-derived polysaccharide of the present invention may be directly used or used in combination with other foods or other food compositions, and may be appropriately used according to a general method. A mixing amount of active ingredients may be appropriately determined according to the purpose of use thereof (the purpose of prevention or health maintenance). Generally, the corn-derived polysaccharide of the present invention may be added in an amount of 0.01 wt % to 70.00 wt %, preferably 0.01 wt % to 30.00 wt %, and more preferably 0.01 wt % to 10.00 wt %, with respect to a total amount of raw materials for preparing a food or a beverage.

The type of food is not particularly limited. The food composition including the corn-derived polysaccharide as an active ingredient may be used in the form of a preparation for oral administration, such as tablets, hard or soft capsules, a liquid, a suspension, or the like, and these preparations may be formulated using a general acceptable carrier, and in the case of preparations for oral administration, may be formulated using, for example, an excipient, a binder, a disintegrant, a lubricant, a solubilizing agent, a suspending agent, a preservative, a bulking agent, or the like.

Examples of foods to which the corn-derived polysaccharide may be added include meat, sausage, bread, chocolate, candies, snacks, confectioneries, pizza, ramen, other noodles, gums, dairy products including ice cream, various soups, beverages, tea, drinks, alcoholic beverages, powder preparations, and vitamin complexes, but the present invention is not limited to the above examples.

Feed Composition

A feed composition including the corn-derived polysaccharide of the present invention as an active ingredient may be fed along with a general feedstuff, and the feed composition of the present invention may be added to a general feed composition to thereby prepare a functional feed composition. In addition, the feed composition of the present invention may further include a functional ingredient, in addition to the corn-derived polysaccharide of the present invention. When a functional feed composition, in which the general feed composition and the corn-derived polysaccharide of the present invention are mixed, is prepared, the corn-derived polysaccharide of the present invention may be added in an amount of 0.01 wt % to 30.00 wt %, preferably 0.01 wt % to 20.00 wt %, with respect to a total amount of the feed composition. An effective dose of the corn-derived polysaccharide of the feed composition may be used in accordance with the effective dose of the food composition, but may be the above-described range or less in the case of long-term administration for the purpose of continuous immune enhancement or health control, and since the active ingredient has no problem in terms of safety, it may also be used in an amount that is equal to or greater than the above-described amount range.

The feed composition of the present invention is intended for livestock or poultry. Examples of the livestock or the poultry include, but are not limited to, cows, pigs, chickens, horses, sheep, donkeys, mules, wild boars, rabbits, quails, domestic ducks, roosters, chickens for cockfighting, pigeons, turkeys, dogs, cats, monkeys, hamsters, mice, rats, hill mynas, parrots, parakeets, and *canaries*, and a subject of the feed composition of the present invention may be any mammal or bird except for humans, which can be domestically raised.

Pharmaceutical Composition

A pharmaceutical composition including the corn-derived polysaccharide of the present invention enhances the immune activity of a subject. The pharmaceutical composition including the corn-derived polysaccharide of the present invention may be a pharmaceutical composition for preventing and treating a disease caused by immune deficiency, immune degradation, or immune system damage. In addition, the pharmaceutical composition including the corn-derived polysaccharide of the present invention may be a pharmaceutical composition for preventing and treating a disease caused by immune degradation through an anticancer therapy such as chemotherapy or radiation therapy or caused by immune degradation after bone marrow transplantation, AIDS caused by immune system damage, and an cancer disease caused by immune degradation.

The pharmaceutical composition of the present invention may include 0.01 wt % to 80 wt %, preferably 0.02 wt % to 65 wt %, of the corn-derived polysaccharide of the present invention. However, the amount of the corn-derived polysaccharide of the present invention may be increased or decreased according to the need of a subject, and may be appropriately increased or decreased according to conditions such as dietary life, nutrition status, disease progression, the degree of obesity, and the like.

The pharmaceutical composition of the present invention may be administered orally or parenterally, and may be used in the form of a general pharmaceutical preparation. A suitable pharmaceutical preparation may be a preparation for oral administration, such as tablets, hard or soft capsules, a liquid, a suspension, or the like, and these pharmaceutical preparations may be formulated using a general pharmaceutically acceptable carrier, for example, in the case of preparations for oral administration, an excipient, a binder, a disintegrant, a lubricant, a solubilizing agent, a suspending agent, a preservative, a bulking agent, or the like.

A dosage of the pharmaceutical composition including the corn-derived polysaccharide of the present invention may be determined by a specialist according to various factors such as conditions, age and gender of patients, complications, and the like, and may generally range from 0.1 mg/1 kg to 10 g/1 kg, preferably 10 mg/1 kg to 5 g/1 kg, for an adult. In addition, the pharmaceutical composition may be included in a daily dosage or a dosage corresponding to ½, ⅓, or ¼ thereof per unit dosage form, and may be administered once to six times a day. However, in the case of long-term administration for the purpose of health and hygiene or for the purpose of health control, the dosage of the pharmaceutical composition may be the above-described amount range or less, and since the active ingredient has no problem in terms of safety, it may also be used in an amount that is equal to or greater than the above-described amount range.

MODE OF THE INVENTION

Advantages, features, and aspects of the present invention will become more apparent with respect to the following examples. However, the present invention is not limited to the examples set forth herein and may be embodied in many different forms. Rather, these examples are provided so that this disclosure will be thorough and complete, and will fully convey the scope of the invention to those of ordinary skill in the art, and the present invention will be defined only by the scope of the appended claims.

<Materials and Methods>

As corn steep liquor (CSL), which is a by-product generated in a corn starch preparation process, CSL produced by Sandol Food Co., Ltd and the HongCheon Institute of Medicinal Herb was used. The CSL is a by-product remaining after producing starch from corn by using sulfurous acid. Wheat-derived arabinoxylan was purchased from Megazyme (Wicklow, Ireland).

<Example 1> Separation of Corn-Derived Immune Polysaccharide

Corn starch is obtained by immersing corn in an aqueous sulfurous acid solution. At this time, corn steep liquor (CSL) and the corn germ portion and pericarp, which have been removed during extraction, are generated as by-products. The CSL was diluted about 3-fold to a final concentration of 20 Brix, and ethanol (EtOH) was added thereto in a volume corresponding to 4 times the final volume and maintained overnight, followed by centrifugation (6,000 rpm, 30 min, 4° C.), thereby collecting a precipitate. The precipitate was denoted as CBP-0. Then, the precipitate, i.e., CBP-0, was precipitated again using a solution prepared by mixing distilled water (DIW) and ethanol in a volume ratio of 1:1, and then collection of the precipitate and the supernatant was repeated three times using a centrifuge (6,000 rpm, 30 min, 4° C.). Subsequently, the collected supernatant was concentrated again using a rotary vacuum concentrator, and then lyophilized to collect the lyophilizate. The collected lyophilizate was denoted as CBP1S and used in an experiment (see FIG. 1).

<Example 2> Purification of Polysaccharide

To identify an active entity of CBP1S, which is the corn-derived polysaccharide precipitate obtained in Example 1, purification of the polysaccharide was carried out according to the following process. First, a CBP1S fraction, which is the lyophilizate of the supernatant separated using a mixed solution of distilled water (DIW) and ethanol in a volume ratio of 1:1, was dissolved in a small amount of water, and then subjected to purification by gel permeation chromatography (GPC) using a Sephadex G-100 column (4 cm×120 cm) equilibrated with a 50 mM ammonium formate buffer (pH 5.5). An eluate obtained as a result of GPC was fractionated into 120 fractions of 5 ml each, and each fraction was subjected to neutral sugar and protein content analysis (see FIG. 2) to recover from 1 kDa to 100 kDa, thereby obtaining a polysaccharide fraction (CBP1S-I) having a molecular weight of 80 kDa (see FIG. 3).

<Example 3> Analysis of Constituent Sugars of CBP0 and CBP1S

A method by Albersheim et al. (Jones T M, Albersheim P. A gas chromatographic method for the determination of aldose and uronic acid constituents of plant cell wall polysaccharides. Plant Physiol. 49: 926-936 (1972)) was partially modified to perform component sugar analysis. Each polysaccharide sample, i.e., the fractions, was hydrolyzed, and then each of a plurality of component sugars was derivatized with alditol acetate to perform gas chromatography (GC) analysis. Specifically, first, each of the polysaccharide samples, i.e., the CBP0 and CBP1S polysaccharide fractions, was hydrolyzed by allowing a reaction to occur in 2M trifluoroacetic acid (TFA) at 121° C. for 1.5 hours, and then the hydrolyzate was dissolved in 1 ml of 1 M $NH_4OH$ (ammonia solution) and reduced with 10 mg of $NaBH_4$ for 4 hours. Then, an appropriate amount of acetic acid was added to the resulting product to remove the remaining $NaBH_4$, followed by repeated drying with methanol to remove excess acetic acid and conversion into an alditol corresponding to each constituent sugar. Subsequently, 1 ml of acetic anhydride was added to each alditol and allowed to react at 121° C. for 30 minutes to convert each alditol into alditol acetate, the resulting alditol acetate was extracted by separation using a chloroform/$H_2O$ two-phase solvent system, and the extract was dried and then dissolved in a small amount of acetone, and was used as a sample for GC analysis. GC analysis conditions of the alditol acetate derivatives are shown in Table 1 below, and mole % of each constituent sugar was calculated by calculating a peak area and molecular weight of each derivative and a molecular response factor for a flame ionization detector (FID).

TABLE 1

| | |
|---|---|
| Apparatus | GC ACME6100 (YoungLin Co. Ltd, Korea) |
| Detector | Flame ionization detector (FID) (YoungLin Co. Ltd., Korea) |
| Column | SP2380 capillary column (Supelco, USA) |
| Column size | 0.25 mm × 30 m, 0.2 mm film thickness |
| Oven temp. | 60° C.(1 min) → 220° C.(12 min) → 250° C.(15 min) 30° C./min 8° C./min |
| Injector temp. | 240° C. |
| Detector temp. | 260° C. |
| Carrier gas | $N_2$ (1.5 mL/min) |

Analysis Conditions of Gas-Liquid Chromatography for Analysis of Constituent Sugars The results thereof are as follows. First, as a result of analyzing the chemical composition of CBP-0 as a crude polysaccharide of CSL, which is a starch by-product, 70.7±0.4% neutral sugars, 0.9±0.3% acidic sugars, and 28.4±0.9% proteins were detected. In addition, CBP-0 was hydrolyzed and converted into an alditol acetate derivative, and as a result of analyzing constituent sugars, CBP-0 included high percentages of glucose (46.8%), arabinose (11.7%), and xylose (7.0%), and trace amounts of mannose and galactose were detected in CBP-0 (see Table 2).

Meanwhile, as a result of examining chemical properties of CBP1S, which is the supernatant fraction obtained by 50% ethanol treatment, CBP1S consisted of 81.0% neutral sugars, 9.5% of acidic sugars, and 9.5% proteins, and did not include a KDO material, which is found in plants. In addition, as a result of analyzing constituent sugars of CBP1S, CBP1S consisted of 33.5% glucose, 22.3% arabinose, and 14.3% xylose, and trace amounts of galactose and mannose were detected.

TABLE 2

| Chemical composition | CBP-0 | CBP-1S (%) |
|---|---|---|
| Neutral sugar | 70.7 ± 0.4 | 81.0 ± 0.1 |
| Uronic acid | 0.9 ± 0.3 | 9.5 ± 0.1 |
| Protein | 28.4 ± 0.9 | 9.5 ± 0.8 |
| KDO-like material | — | — |
| Component sugar | | (Mole %) |
| Rhamnose | — | — |
| Fucose | — | — |
| Arabinose | 11.64 ± 0.7 | 22.3 ± 0.2 |
| Xylose | 7.04 ± 0.5 | 14.3 ± 0.0 |
| Mannose | 1.0 ± 0.1 | 1.4 ± 0.0 |
| Galactose | 4.24 ± 0.0 | 9.5 ± 0.0 |
| Glucose | 46.78 ± 0.5 | 33.5 ± 0.2 |
| GalA + GlcA | 0.9 ± 0.3 | 9.5 ± 0.1 |

Chemical properties of CBP-0 and CBP1S separated from corn and CSL

<Example 4> Measurement of Molecular Weight Distribution of CBP-0 and CBP1S

To measure the molecular weight distribution of CBP-0 and CBP1S, which were purified from starch by-products, high performance liquid chromatography (HPLC) was performed using a Superdex 200 GL column.

As a result, in the case of CBP-0, which is a crude saccharide separated from a starch by-product, it was confirmed that CBP-0 consisted of a mixture of a high molecular weight material and a low molecular weight material. In addition, as a result of examining the molecular weight distribution of CBP1S, CBP1S mostly included a low-molecular fraction at higher proportion compared to CBP-0 (see FIG. 4). However, as a lower molecular weight material has higher reactivity with an RI detector of HPLC, it was determined that CBP1S generally consisted of a mixture of high and low molecular weight materials.

<Example 5> Activity of Macrophage

The cytokine production of macrophages by direct stimulation of corn starch by-product-derived polysaccharide samples was measured in vitro. A specific measurement method is as follows. First, a polysaccharide sample solution prepared using PBS to a concentration of 2,000 μg/ml was serially diluted 10-fold by adding RPMI 1640 thereto, to a concentration ranging from 1,000 μg/ml to 1 μg/ml and 100 μl/well of the resulting sample solution was distributed into a flat bottomed 96-well microplate. 1 ml of a 5% thioglycollate medium was injected into the abdominal cavity of BALB/c (female, 6 weeks) mice, macrophages induced for 72 hours were collected from the abdominal cavity of each mouse and washed, and the number of cells ($2.5 \times 10^6$ cells/ml of RPMI 1640) was adjusted to prepare a macrophage suspension, and 100 μl of the macrophage suspension was added to each well and incubated in a 5% $CO_2$ incubator at 37° C. for 24 hours. After incubation was completed, centrifugation was performed at 1,500 rpm and 4° C. for 5 minutes, 150 μl of a cell culture was collected, and the contents of induced cytokines in the supernatant were measured.

The contents of cytokines produced by the macrophages were analyzed by sandwich enzyme-linked immunosorbent assay (sandwich ELISA). An antibody against each cytokine was diluted in a coating buffer to be coated onto a flat-bottomed 96-well microplate, and then the resulting microplate was maintained at 4° C. for 12 hours. The coated microplate was washed three times with a washing buffer (PBS with 0.05% Tween 20, PBST), 200 μl of an assay diluent (PBS with 10% FBS or 2% skim milk) was added thereto, the resulting microplate was maintained for 1 hour, and surfaces of the wells to which the antibody was not bound were blocked. After blocking was completed, each well was washed again three times with a washing buffer, 50 μl of a serially diluted reference material (recombinant mouse cytokine) and 50 μL of an immune cell culture were dispensed into each well. The resulting microplate was maintained at room temperature for 2 hours and washed with a washing buffer, and the resulting cells were treated with 100 μl of a detection antibody (in assay diluent), maintained at room temperature for 1 hour, and then washed again. After washing, the resulting cells were treated with 100 μl of an enzyme reagent (avidin-horseradish peroxidase conjugate), binding therebetween was allowed at room temperature for 30 minutes, 100 μl of a substrate solution [tetramethylbenzidine (TMB) and hydrogen peroxide) was added thereto, and then the resulting solution was allowed to react in a dark place for 30 minutes, followed by treatment with 50 μl of a stop solution [(1 M $H_3PO_4$) or (2 N $H_2SO_4$)] and measurement of absorbance at 450 nm.

As a result, it was confirmed that CBP-0 and CBP1S, which are active polysaccharides, accelerated the production of IL-6, IL-12, and TNF-α (see FIG. 5). In particular, it was confirmed that in the case of CBP1S separated from CBP-0, the productivity of IL-6, IL-12, and TNF-α was maintained at high levels from a high concentration, i.e., 1,000 μg/ml, to a low concentration, i.e., 10 μg/ml (see FIG. 5). From these results, it was confirmed that the CBP-0 active polysaccharide was mainly present in CBP1S. Afterwards, an additional analysis experiment for CBP1S was conducted.

<Example 6> Evaluation of Anti-complementary Activity of CBP-0 and CBP1S

Blood was collected from healthy adults and maintained at room temperature for about 15 minutes to be coagulated, and then the coagulated blood was cleaved and maintained at room temperature for about 5 minutes. The resulting blood was maintained again at 4° C. for about 20 minutes, and then centrifuged (2,200 rpm, 15 min, 4° C.) to separate serum therefrom, and 1 ml of the serum was distributed into each microcentrifuge tube and freeze-stored at −70° C. for use in an experiment.

The anti-complementary activity was measured using a complement fixation test method based on a degree of erythrocyte hemolysis due to a complement remaining after complement consumption by the sample using a Meyer method.

Samples dissolved in distilled water at various concentrations were mixed with 50 µl of each of a gelatin veronal buffer (GVB++, pH 7.4, containing 0.1% gelatin, 0.15 mM Ca++, and 0.5 mM Mg++) and serum from normal individuals to allow a primary reaction to occur at 37° C. for 30 minutes. 350 µl of GVB++ was added to the reaction solution, the resulting solution was serially diluted 10-fold to 160-fold, and 750 µl of GVB++ and 250 µl of IgM-sensitized sheep erythrocytes (EA cells, 1×108 cells/ml) were added thereto to allow a secondary reaction to occur at 37° C. for 60 minutes, and 2.5 ml of phosphate buffered saline (PBS, pH 7.4) was then added thereto to stop the reaction. The reaction solution was centrifuged at 2,000 rpm for 10 minutes to obtain a supernatant, and absorbance of the supernatant was measured at 412 nm for the measurement of residual hemolytic activity. The anti-complementary activity was expressed as inhibition of 50% total complement hemolysis (ITCH50, %) with respect to 50% total complement hemolysis (TCH50, %) of a negative control treated only with normal human serum, GVB++, and distilled water. As a positive control, polysaccharide-K (PSK), which is a Coriolus versicolor-derived immune-stimulant, was used for comparison.

The degree of activation of the negative control was expressed as ITCH50 0% and the activity of each of the CBP-0 and CBP1S samples was examined, and as a result of examination, the active polysaccharide CBP-0 exhibited, at a concentration of 1,000 µg/ml, an activity corresponding to 50% of that of the positive control added at the same concentration, whereas CBP1S exhibited, at a concentration of 1,000 µg/ml, an excellent anti-complementary activity corresponding to the that of the positive control added at the same concentration (see FIG. 6). PSK, as a positive control, is an immunologically active polysaccharide currently commercially available as an anti-cancer agent, and since it is generally known that pharmacological properties of polysaccharides exhibiting 50% anti-complementary activity or more at a concentration of 1,000 µg/ml are generally accepted, it was confirmed that CBP1S exhibited excellent complementary activity.

<Example 7> Evaluation of Ability of CBP-0 to Kill Tumor Cells by Natural Killer Cells 1,000 µg of a CBP-0 polysaccharide sample separated from a starch processing by-product was injected intravenously into BALB/c (6 weeks, female) mice, and after 3 days, the mice were sacrificed by cervical dislocation to aseptically remove the spleen from each mouse. Each spleen was ground (100 mesh) and filtered (200 mesh) on PBS using a stainless steel mesh to obtain splenocytes. 5 ml of 0.2% NaCl was added to the splenocytes for 15 seconds to 30 seconds to destroy the residual erythrocytes, and the resulting cells were washed two to three times with a serum-free medium, subjected to adjustment of the number of cells to 1×10$^6$ cells/ml, and used as effector cells. YAC-1 tumor cells, which are highly susceptible to natural killer cells, were used as target cells, and the effector cells and the target cells were added to a round-bottomed 96-well microplate in a ratio (E/T ratio) of 100, 50, and 25. The resulting cells were incubated in a 5% $CO_2$ incubator at 37° C. for 6 hours, and then the amount of generated lactate dehydrogenase (LDH) released from the target cells by the killing ability of the effector cells was measured using EZ-LDH (Dogen, Seoul, Korea). At this time, the ability of natural killer cells to kill tumor cells was calculated by Equation 1 below:

NK cell activity (%)=[(experimental secretion amount−natural secretion amount)/(maximum secretion amount-natural secretion amount)]× 100  <Equation 1>

As a result, it was confirmed that splenocytes (NK-cells) obtained by intravenously injecting 1,000 µg of CBP-0 exhibited a higher ability to kill tumor cells as the ratio (E/T ratio) of the effector cells (splenocytes) to the target cells (YAC-1) increased. In particular, the killing ability of natural killer cells was observed to be the most active at E/T=100. In addition, similarly, IFN-γ and granzyme, which are marker substances secreted from NK cells, were observed to have the highest activity at E/T=100 (see FIG. 7). Thus, it was confirmed that CBP-0, which is a polysaccharide derived from a corn starch by-product, contributed to the activation of NK cells having the ability to kill tumor cells, and, accordingly, it was determined that CBP-0, which is a polysaccharide derived from a corn starch by-product, would have anticancer activity by the activation of NK cells.

<Example 8> Anti-metastasis Activity of CBP1S on Tumor Cells

The anti-metastasis activity of the sample was evaluated using an experimental animal tumor metastasis model using Colon 26-M3.1 carcinoma, which is a highly metastatic lung tumor cell line. To observe a tumor metastasis effect of the sample, the sample was orally administered to experimental animals twice a day for 15 days at intervals of 12 hours according to each concentration, and then Colon 26-M3.1 lung carcinoma cells (3×10$^4$ cells/mouse) were intravenously injected into BALB/c mice. 14 days after tumor inoculation, the mice were sacrificed and the lungs, which are the target organ of the tumor cells, were removed and the metastasized tumor was fixed in Bouin's solution (Sigma), and then the number of colonies of the metastasized tumor was counted. The anti-tumor metastasis effect of the sample was compared with a control inoculated only with the tumor. That is, the anti-metastasis activity of the sample was evaluated compared to the control that had not been administered the sample and exhibited 100% metastasis of the tumor.

As a result, only about 70% metastasis proceeded in a group administered 1,000 µg of CBP1S, from which it was confirmed that the CBP1S sample had an excellent anti-metastasis effect, i.e., 30%. However, no significant anti-metastasis activity was observed in groups administered 10

µg and 100 µg of CBP1S. From the above results, it was confirmed that the CBP1S sample was effective in inhibiting tumor metastasis when administered at a concentration of 1,000 µg.

<Example 9> Evaluation of Macrophage Activity of CBP1S-I, CBP1S-II, and CBP1S-III The macrophage activity of CBP1S-I, CBP1S-II, and CBP1S-III was evaluated. This was evaluated through the ability to induce macrophage cytokine production, and specific evaluation was carried out in the same manner as in Example 4 above.

As a result, it was confirmed that CBP1S-I maintained the productivity of IL-6, IL-12, and TNF-α at high levels from a high concentration, i.e., 1,000 µg/mL to a low concentration, i.e., 10 µg/mL, whereas CBP1S-II and CBP1S-III did not exhibited such a pattern (see FIG. 9). Thus, it was confirmed that the CBP1S active polysaccharide having macrophage activity was mainly present in CBP1S-I. Therefore, a subsequent structural analysis experiment was performed on CBP1S-I.

<Example 10> Analysis of Constituent Sugars of CBP1S-I, CBP1S-II, and CBP1S-III

The constituent sugars of CBP1S-I were analyzed to determine general chemical properties thereof. At this time, specific analysis was performed in the same manner as in Example 2 above.

As a result, CBP1S-I consisted of 88.9% neutral sugars and 9% acidic sugars, and contained small amounts of proteins and KDO materials detected in plant extracts. Meanwhile, CBP1S-I, CBP1S-II, and CBP1S-III were hydrolyzed to be converted into alditol acetate derivatives and constituent sugars thereof were analyzed, and as a result, CBP1S-I included high percentages of arabinose and xylose, i.e., 37.9% and 29.8%, respectively, and also included small amounts of glucose, uronic acid, and other constituent sugars (see Table 3). These results strongly suggest that CBP1S-I may contain a high percentage of arabinoxylan, which is a type of hemicellulose among cell wall polysaccharides present in corn.

TABLE 3

| Chemical composition | CBP1S-I | CBP1S-II | CBP1S-III (%) |
|---|---|---|---|
| Neutral sugar | 88.9 ± 1.8 | 78.9 ± 0.3 | 61.7 ± 0.1 |
| Uronic acid | 9.0 ± 0.3 | 8.6 ± 0.3 | — |
| Protein | 1.4 ± 0.9 | 11.2 ± 0.3 | 32.5 ± 0.4 |
| KDO-like material | 0.7 ± 0.1 | 1.4 ± 0.1 | 5.8 ± 0.1 |
| Component sugar | | | (Mole %) |
| Rhamnose | — | — | — |
| Fucose | — | — | — |
| Arabinose | 37.9 ± 0.3 | 20.1 ± 0.2 | 9.0 ± 0.3 |
| Xylose | 29.8 ± 0.4 | 19.3 ± 0.3 | 9.7 ± 0.2 |
| Mannose | 0.8 ± 0.0 | 1.5 ± 0.0 | 2.8 ± 0.1 |
| Galactose | 9.2 ± 0.2 | 9.0 ± 0.0 | 6.1 ± 0.1 |
| Glucose | 11.4 ± 0.3 | 29.0 ± 0.3 | 34.2 ± 0.3 |
| GalA + GlcA | 9.0 ± 0.3 | 8.6 ± 0.3 | — |

Chemical Properties of CBP1S-I, CBP1S-II, and CBP1S-III Separated from CBP1S

<Example 11> Structural Analysis of CBP1S-I

<11-1> Preparation of Methylsulfinyl Carbanion

To prepare methylsulfinyl carbanion, 20 ml of anhydrous dimethylsulfoxide (DMSO) was added to 1.26 g of anhydrous NaH, and then the resulting mixture was filled with nitrogen and allowed to react in an oil bath at 90° C. for about 10 minutes to about 15 minutes. The time at which the reaction solution turned pale green was denoted as a termination point, the reaction was terminated at that time, followed by cooling to room temperature and centrifugation at 3,000 rpm and 30° C. The supernatant including methylsulfinyl carbanion was subjected to nitrogen substitution to avoid contact with air, divided into small amounts and stored frozen for use.

<11-2> Methylation

Methylation for determining a binding position of the polysaccharide sample was performed using a Hakomori method (Hakomori, S. A. (1964) A rapid permethylation of glycolipid and polysaccharide catalyzed by methylsulfinyl carbanion in dimethyl sulfoxide. J. Biochem. 55: 205-208). 1 ml of anhydrous DMSO was added to each polysaccharide sample (0.5 mg) which had been sufficiently dried in a desiccator for 1 day to 2 days, and stirred to completely dissolve the sample therein, and 500 µl of methylsulfinyl carbanion (MSCA) was added thereto to allow a reaction to occur for 4 hours. At this time, as needed, MSCA was further added so that the polysaccharide could be completely converted into polyalkoxide, and the presence or absence of remaining unreacted MSCA was identified with triphenylmethane. The sample converted into polyalkoxide was methylated by adding an excess of CH3I thereto, and the remaining CH3I was removed through $N_2$ gas flushing, followed by collection using a Sep-pak C18 cartridge.

<11-3> Hydrolysis and Acetylation of Methylated Polysaccharide

The methylated sample was hydrolyzed by adding 1 ml of 2M TFA thereto and allowing a reaction to occur at 121° C. for 1.5 hours, and then dried. The hydrolyzed sample was dissolved in ethanol to which a few drops of 25% $NH_4OH$ had been added, and 10 mg of $NaBH_4$ was added thereto for ring opening and reduction for 4 hours, and an appropriate amount of acetic acid was added to remove the remaining $NaBH_4$ and the resulting solution was repeatedly dried while adding methanol thereto to remove the excess acetic acid. Subsequently, 1 ml of acetic anhydride was added thereto and a reaction was allowed to occur at 121° C. for 3 hours to convert the resulting sample into partially methylated alditol acetate, followed by separation and extraction with a two-phase solvent system (chloroform, $H_2O$), dissolution in acetone, and GC and GC-MS analysis.

<11-4> GC and GC-MS Analysis of Partially Methylated Alditol Acetate

The GC analysis was performed using Young-Lin ACME-6100 GC equipped with a SP-2380 capillary column (0.25 mm×30 m, 0.2 mm film thickness, Supelco) under optimum temperature conditions [60° C. (1 min), 60° C.→180° C. (30° C./min), 180° C.→250° C. (1.5° C./min), 250° C. (5 min)] in a splitless injection mode (¹/₂₀). At this time, the flow rate of a carrier gas ($N_2$) was adjusted to be 1.5 ml/min. Meanwhile, the GC-MS analysis was performed using an Agilent 6890N GC system equipped with a SP-2380 capillary column (0.2 mm film, 0.25 mm i.d.×30 m, Supelco, Bellefonte, Pa., USA) and a 5973N mass spectrophotometer (Agilent Technologies, Palo Alto, Calif., USA) under the same optimum temperature conditions as those of the GC analysis in a splitless injection mode (He flow rate: 1.5 ml/min). Derivatives of the methylated samples were identified by a combination of GC-MS fragment ion analysis and a GC relative retention time, and the molar % of each peak was converted from a peak area and a molecular response factor.

As a result, CBP1S-I, which is a corn starch processing by-product polysaccharide, was confirmed to have a total of 8 sugar chains participating in binding and high percentages of arabinose and xylose bonds. In particular, in the case of arabinose residues, terminal-Araf was detected at a high percentage (12.2%), from which it was assumed that many arabinose residues were present at the non-reducing terminal, and thus the arabinose residues were highly branched in a side chain. From the fact that 2-linked-Araf and 5-linked-Araf were present at high percentages, it was assumed that the side chain consisting of arabinose constituted a non-reducing terminal in the form of linkage via a (1→2) bond and a (1→5) bond (see Table 4).

Meanwhile, in the case of xylose residues, xylose present at the non-reducing terminal was barely detected, whereas 4-linked Xylp, 3,4-branched Xylp, and 2,3,4-branched Xylp were detected at high percentages. From these results, it was assumed that the main chain of CBP1S-I was present in the form of xylan of (1→4) binding, and a single side chain was branched therefrom at the C3 position of xylose or two side chains were simultaneously branched therefrom at the C2 and C3 positions of xylose. In particular, CBP1S-I, which is a polysaccharide derived from a corn starch by-product, exhibited a unique pattern, particularly detection of 2,3,4-linked Xylp residues at a high percentage, from which it was confirmed that CBP1S-I had a form in which arabinose residues were linked via two side chains to a xylose main chain linked by a (1→4) bond.

These results suggest that many more side chains consisting of arabinose were present in the case of arabinoxylan extracted from a corn starch processing by-product than in the case of commercially available wheat arabinoxylan (see FIG. 10). In addition, it was confirmed that the arabinan side chain branched from the xylan main chain is relatively long compared to commercially available wheat arabinoxylan. Thus, it was finally concluded that CBP1S-I, which is an immunologically active polysaccharide derived from a corn starch by-product, results from highly branched arabinoxylan. Meanwhile, as a result of analyzing methylation of arabinoxylan extracted from a corn starch processing by-product of the present invention, it was confirmed that the number of arabinose terminals was detected in a significantly decreased number compared to the number of xylose side chains, from which it was assumed that other saccharides were bound to the terminal of an arabinan side chain.

TABLE 4

| [Glycosyl linkage composition] | | |
|---|---|---|
| Glycosyl residue | Deduced linkage | Mole % CBP1S-1 |
| Arabinose (f) | Terminal (f) | 12.2 |
|  | 2 | 2.0 |
|  | 5 | 2.3 |
| Xylose (p) | Terminal (p) | 1.8 |
|  | 4 | 9.1 |
|  | 3 | 3.4 |
|  | 3, 4 | 18.7 |
|  | 2, 3, 4 | 6.6 |

Methylation Analysis of CBP1S-I Purified from CBP1S

<Example 12> Analysis of Detailed Structure of CBP1S-I

The detailed structure of CBP1S-I, confirmed to increase the secretion of cytokines in Example 9, was analyzed.

<12-1> Preparation of Fragment by Endo-1,4-β-D-Xylanase 20 mg of CBP1S-I was dissolved in a 0.1 M sodium phosphate buffer (pH 6.5), and then hydrolyzed in a thermostatic bath at 43° C. for 72 hours after adding 10 units of endo-1,4-β-D-xylanase (from Cellvibrio mixtus, Megazyme International Ireland Ltd., Wicklow, Ireland) thereto, followed by heating in boiling water at 100° C. for 30 minutes to inactivate the remaining enzyme. The reaction product was centrifuged to remove the precipitated inactive enzyme protein, and the supernatant was fractionated on HPLC using a Superdex 200 GL column equilibrated with 50 mM ammonium formate buffer (pH 5.5), followed by neutral sugar content analysis. At this time, three fractions, i.e., CBP1S-I-A, CBP1S-I-B, CBP1S-I-C, were obtained and lyophilized to prepare endo-1,4-β-D-xylanase-treated fractions (see FIG. 11).

<12-2> Matrix-Assisted Laser Desorption Ionization-Time of Flight (MALDI-TOF) Analysis For molecular weight measurement by MALDI-TOF, a matrix was prepared by dissolving 10 mg/ml of 2,3,4-trihydroxyacetophenone (THAP) in a mixed solution of 0.1% TFA-containing distilled water and acetonitrile (ACN) in a volume ratio (v/v) of 1:1. The matrix solution was mixed with the sample in a volume ratio of 1:1, and then 1 μl of the resulting mixture was added dropwise to a MALDI target plate and dried, and the molecular weight of the sample was obtained at an acceleration voltage of 25 kV using an UltraflexIII TOF/TOF instrument (Bruker Daltonics, Bremen, Germany).

MALDI-TOF analysis was performed to identify the accurate molecular weight of an oligosaccharide constituting CBP1S-I-C and predict the structure thereof. As a result of performing MALDI-TOF using 2,3,4-THAP as a matrix, various types of molecular weight peaks were observed. First, the molecular weight of m/z 833 [P6+Na]+, assumed to be the simplest binding, was determined to be Na+ ions (MW: 23) added to 6 pentose residues [P=(132*6)+18]. In addition, m/z 965, 1097, 1229, and 1361 peaks, in which a pentose residue was sequentially added by an increment of (+132) to the molecular weight of m/z 833, were observed, and the peaks correspond to [P7+Na]+, [P8+Na]+, [P9+Na]+, and [P10+Na]+(see FIG. 12). Second, the molecular weight of m/z 759 [P4+M+Na]+ was determined to be 1 unit of 4-methyl-glucuronic acid (MW: 190) bound to 4 pentose residues [P=(132*4)+18] and Na+ ions (MW: 23) added thereto, and afterwards, molecular weight peaks in which a pentose was added one by one were also observed (see FIG. 13). Third, the molecular weight of m/z 731 [P4+H+Na]+ was determined to be 1 hexose (MW: 162) bound to 4 pentose residues [P=(132*4)+18] and Na+ ions (MW: 23) added thereto (see FIG. 14). Fourth, the molecular weight of m/z 741 [P+Acf+Na]+ was determined to be 2 units of acetyl ferulic acid (Acf: 176+42) bound to 2 pentose residues [P=(132*2)+18] and Na+ ions (MW: 23) added thereto (see FIG. 15). Lastly, the molecular weight of m/z 713 [P+M+Acf+Na]+ was determined to be 1 unit of 4-methyl-glucuronic acid (MW: 190) and 1 unit of acetic ferulic acid (Acf: 176+42) bound to 2 pentose residues [P=(132*4)+18] and Na+ ions (MW: 23) added thereto (see FIG. 16). From the above results, it was confirmed that arabinoxylan, which is separated from a corn starch by-product, had a structure in which 4-methyl-glucuronic acid and acetyl ferulic acid, which are generally not frequently detected in plant polysaccharides, were bound to a side chain terminal thereof.

<Example 13> Analysis of Overall Structure of Active Polysaccharide CBP1S-I

An overall structure of CBP1S-I, which was confirmed to increase the secretion of cytokines in Example 9 above, was analyzed. The overall structure of CBP1S-I was schematized based on the analysis of sugar chain binding patterns by methylation analysis of CBP1S-I, which is an immunologically active polysaccharide of a starch by-product, and information obtained through the enzyme treatment process (see FIG. 17). CBP1S-I is a polysaccharide having a molecular weight of about 80 kDa and consists of a total of about 600 sugars.

Characteristics of a final structure of CBP1S-I, which is an immunologically active polysaccharide of a starch by-product, are as follows: ① xylan in which xylose residues are linked to each other via (1→4) bonds constitutes a main chain, wherein most of the main chain is present such that a single side chain is linked to the main chain at the C3 position of xylose or two side chains are simultaneously linked to the main chain at the C2 and C3 positions of xylose; ② the side chain structure is present such that arabinose is linked in a monosaccharide form, or arabinose residues are linked at the C2, C3, or C5 position; ③ 4-methyl-glucuronic acid, acetic ferulic acid and hexose are bound to the arabinose terminal. Thus, it was confirmed that the immune activity of corn starch by-products is due to arabinoxylans in which arabinose and a specific sugar are highly branched.

<Comparative Example 1> Evaluation of Macrophage Activity of Wheat-derived Arabinoxylan The macrophage activity of wheat-derived arabinoxylan was evaluated. This was evaluated through the ability to induce macrophage cytokine production, and specific evaluation was performed in the same manner as in Example 4 above.

As a result, it was confirmed that the wheat-derived arabinoxylan did not enhance the productivity of IL-6, IL-12, and TNF-α regardless of concentration (see FIG. 18). Thus, it was confirmed that all arabinoxylans do not have an immuno-enhancing ability.

<Comparative Example 2> Structural Analysis of Wheat-derived Arabinoxylan

The structure of wheat-derived arabinoxylan was analyzed in the same manner as in Example 11. The results thereof are shown in Table 5 below and FIG. 19.

TABLE 5

[Glycosyl linkage composition]

| Glycosyl residue | Deduced linkage | Mole % |
| --- | --- | --- |
| Arabinose | Terminal (f) | 9.9 |
|  | 2 | 1.7 |
|  | 3 | — |
|  | 5 | 1.8 |

TABLE 5-continued

[Glycosyl linkage composition]

| Glycosyl residue | Deduced linkage | Mole % |
| --- | --- | --- |
| Xylose | Terminal (p) | — |
|  | 4 | 17.0 |
|  | 3, 4 | 21.7 |
|  | 2, 3, 4 | 17.9 |

Methylation Analysis of Wheat-Derived Arabinoxylan

INDUSTRIAL APPLICABILITY

The present invention relates to an immuno-enhancing composition including a corn-derived polysaccharide. The immuno-enhancing composition may be a food composition, a feed composition, or a pharmaceutical composition.

The invention claimed is:

1. A food composition comprising a separated polysaccharide, wherein
the separated polysaccharide is a polysaccharide separated from a corn steep liquor, and the corn steep liquor is obtained from sulfurous acid treatment of corn,
the polysaccharide comprises arabinose to which 4-methyl-glucuronic acid is linked at a terminal thereof,
the polysaccharide comprises arabinose and xylose in an amount of 8 wt % or more, the polysaccharide comprises xylan, in which xylose residues are linked to each other by a (1→4) bond, as a main chain, and comprises a single side chain linked at a C3 position of the xylose residue or two side chains linked at C2 and C3 positions of the xylose residue, wherein the side chain comprises arabinose,
the polysaccharide comprises arabinose to which acetic ferulic acid, or a hexose is linked at a terminal thereof, and
the polysaccharide is capable of enhancing immunity.

2. The food composition of claim 1, wherein the corn is corn kernels or a by-product thereof.

3. The food composition of claim 1, wherein the polysaccharide has a molecular weight of about 80 kDa.

4. The food composition of claim 1, wherein the polysaccharide increases the secretion of interleukin-6, interleukin-12, or TNF-alpha.

5. The food composition of claim 1, wherein the polysaccharide enhances the activity of natural killer cells.

6. A pharmaceutical composition comprising a separated polysaccharide, wherein
the separated polysaccharide is a polysaccharide separated from a corn steep liquor, and the corn steep liquor is obtained from sulfurous acid treatment of corn,
the polysaccharide comprises arabinose to which 4-methyl-gluconic acid is linked at a terminal thereof,
the polysaccharide comprises arabinose and xylose in an amount of 8 wt % or more,
the polysaccharide comprises xylan, in which xylose residues are linked to each other by a (1→4) bond, as a main chain, and comprises a single side chain linked at a C3 position of the xylose residue or two side chains linked at C2 and C3 positions of the xylose residue, wherein the side chain comprises arabinose,
the polysaccharide comprises arabinose to which acetic ferulic acid, or a hexose is linked at a terminal thereof, and
the polysaccharide is capable of enhancing immunity in a patient having a disease selected from the group consisting of a disease caused by immune deficiency, immune degradation, or a disease caused by immune system damage, immune degradation due to an anti-cancer therapy, immune degradation due to bone marrow transplantation, AIDS caused by immune system damage, and cancer caused by immune degradation.

7. A method for enhancing immunity, comprising administering the food composition according to claim 1 to a subject.

8. The method of claim 7, wherein the subject is a human.

* * * * *